United States Patent
Belikov et al.

(10) Patent No.: US 8,956,343 B2
(45) Date of Patent: Feb. 17, 2015

(54) DENTAL SURGICAL LASER WITH FEEDBACK MECHANISMS

(75) Inventors: Andrei V. Belikov, St. Petersburg (RU); Felix I. Feldchtein, Framingham, MA (US); Gregory B. Altshuler, Lincoln, MA (US)

(73) Assignee: Laser Abrasive Technologies, LLC, Walpole, MA (US)

(*) Notice: Subject to any disclaimer, the term of this patent is extended or adjusted under 35 U.S.C. 154(b) by 36 days.

(21) Appl. No.: 13/379,916

(22) PCT Filed: Dec. 31, 2010

(86) PCT No.: PCT/US2010/062645
§ 371 (c)(1),
(2), (4) Date: Dec. 21, 2011

(87) PCT Pub. No.: WO2011/082383
PCT Pub. Date: Jul. 7, 2011

(65) Prior Publication Data
US 2012/0123399 A1   May 17, 2012

Related U.S. Application Data

(60) Provisional application No. 61/291,608, filed on Dec. 31, 2009.

(51) Int. Cl.
*A61B 18/20* (2006.01)
*A61C 1/00* (2006.01)
*A61B 18/28* (2006.01)
*A61B 17/00* (2006.01)
*A61B 18/22* (2006.01)
*A61B 18/00* (2006.01)

(52) U.S. Cl.
CPC ..... *A61B 18/201* (2013.01); *A61B 2017/00017* (2013.01); *A61B 18/20* (2013.01); *A61B 18/22* (2013.01); *A61B 2017/00057* (2013.01); *A61B 2017/00084* (2013.01); *A61B 2018/00636* (2013.01); *A61B 2018/00642* (2013.01); *A61C 1/0046* (2013.01); *A61B 18/28* (2013.01)
USPC .......................................................... 606/2

(58) Field of Classification Search
USPC ...................................... 606/2–19; 607/88–94
See application file for complete search history.

(56) References Cited

U.S. PATENT DOCUMENTS

| | | |
|---|---|---|
| 5,057,099 A | 10/1991 | Rink |
| 2005/0113815 A1* | 5/2005 | Ritchie et al. .................. 606/15 |
| 2005/0245917 A1 | 11/2005 | Strassl et al. |
| 2005/0256516 A1 | 11/2005 | Boutoussov |
| 2008/0262577 A1 | 10/2008 | Altshuler et al. |

FOREIGN PATENT DOCUMENTS

| | | |
|---|---|---|
| WO | 90/04949 A1 | 5/1990 |
| WO | 2009/003014 A2 | 12/2008 |

OTHER PUBLICATIONS

International Search Report, mailed on Sep. 27, 2011, from International Application No. PCT/US2010/062645, filed on Dec. 31, 2010.
Written Opinion of the International Searching Authority, mailed on Sep. 27, 2011, from International Application No. PCT/US2010/062645, filed on Dec. 31, 2010.

* cited by examiner

*Primary Examiner* — Aaron Roane
(74) *Attorney, Agent, or Firm* — Patentbar International, P.C.

(57) ABSTRACT

A surgical device based on the concept of controlling the laser power during laser surgery based on optical and other signals from the tip and the tissue is described. A laser surgical system generally comprises several basic components, such as a laser, a delivery system, a tip and a control system. A tip may be considered as a particular case of a thermo-optical tip (TOT). TOT is an optical and mechanical element which could be used to modify or treat soft and hard tissues, including cutting, coagulation, vaporization, carbonization, and ablation of tissues.

18 Claims, 21 Drawing Sheets

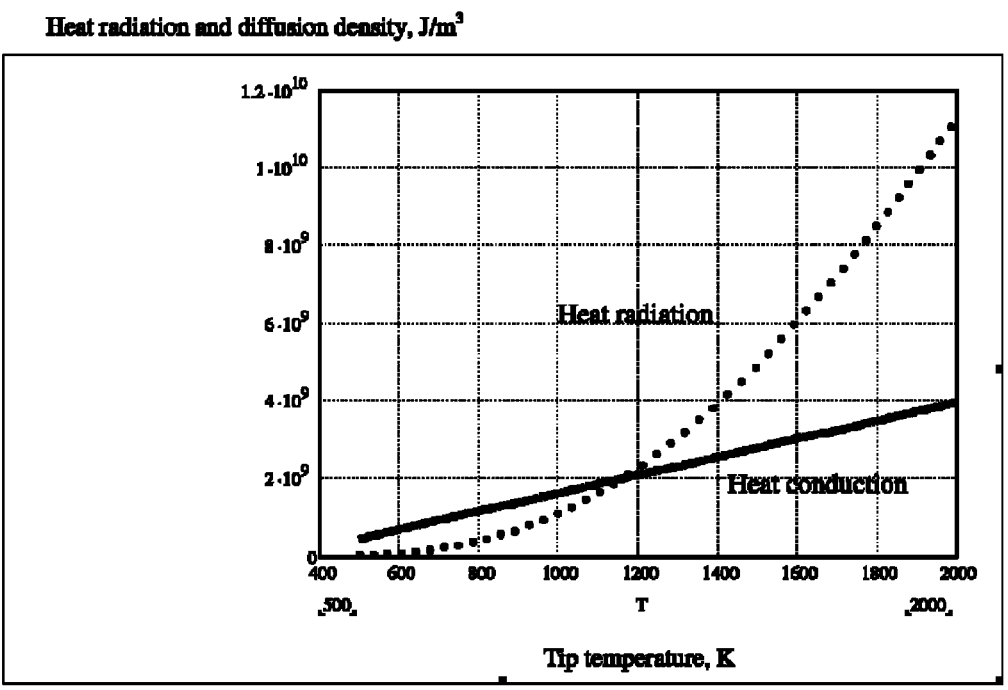
Fig. 7a (2 mm/sec)
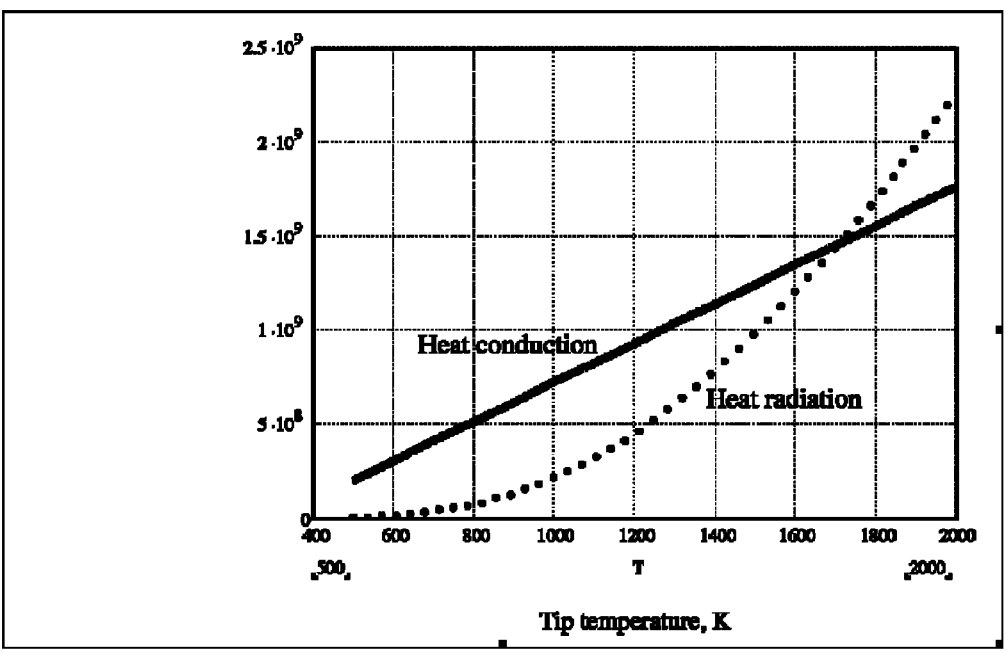
Fig. 7b (10 mm/sec)

Cone 901
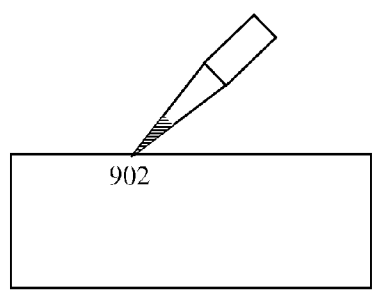
Cylinder 903
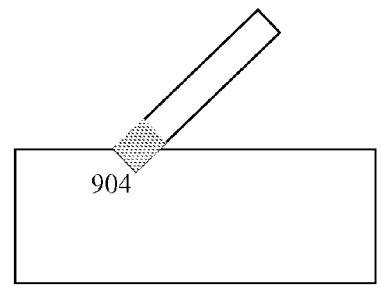
Wedge 905
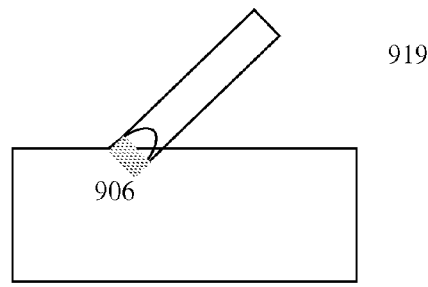
Knife 907
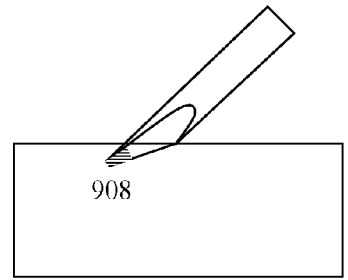
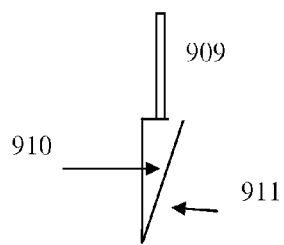
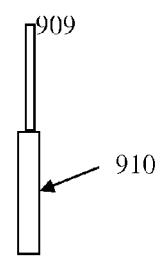
Fig 9

DENTAL SURGICAL LASER WITH FEEDBACK MECHANISMS

CROSS-REFERENCE TO RELATED APPLICATION

This Application is a U.S. National Stage Under 35 USC 371 of International Application PCT/US2010/062645 filed Dec. 31, 2010 which claims priority to a U.S. provisional application No. 61/291,608 filed Dec. 31, 2009, both of which are incorporated herein by reference in their entirety.

FIELD OF THE INVENTION

The present invention is related to the area of surgical treatment of soft and hard oral tissue using laser radiation.

BACKGROUND OF THE INVENTION

Laser surgery, and in particular laser surgery of soft oral tissues is broadly accepted in current practice because of several advantages of laser scalpel over traditional cold scalpels or other surgical means such as electrosurgery. Laser surgery advantages include reduced pain and need for anesthesia, reduced postoperational discomfort, instant tissue coagulation and hemostasis, and automatic sterilization of the operation field.

The most affordable and popular types of dental surgical lasers operate in the near infrared spectral wavelength range of 810 to 1100 nm due to technical progress in semiconductor GaAs lasers which made it possible to generate sufficient laser power in relatively low-cost, simple, reliable, and energy-efficient semiconductor devices. It is well known that light absorption in the biotissue is relatively low in this spectral range and insufficient to produce localized tissue cutting with minimal collateral damage of normal tissue.

Therefore, the dominat mechanism of the laser surgery in this spectral range is associated with so called "hot tip", when optical tip or just the distal end of a fiber optic light delivery system absorbs laser light due contaminated to the tip carbonized tissue, black paper, corn or other material, heats to a high temperature and then performs surgical action because of that high temperature and heat conduction from the "hot tip" to the tissue, rather than by direct interaction of the laser light with the tissue. Such behavior of a laser scalpel tip is typical for contact surgery with different wavelength. The tissue in contact with distal end of the tip is exposed to a high power density and generates heat which can heat up the tip due to heat conduction. The tip is becomes hot, and temperature of the contact tip during surgery can be elevated to 1500° C. or higher. As a result, the tip may melt during surgery and be destroyed.

Due to these phenomena, the cutting efficiency and thermal effect on the tissue during surgery experience uncontrollable change which can result in lack of confidence for surgeons and can be the reason for excessive collateral tissue damage and post-surgery complications. Non-contact surgery is more predictable but it is less convenient for surgeons because it requires a different and new non-tactile skill and art. Also, non-contact surgery requires lasers with wavelengths in the range of 1.8-11 microns which are highly absorbed in the tissue and are substantially more expensive than GaAs diode lasers.

SUMMARY OF THE INVENTION

The present invention is a surgical laser device comprising a source of laser radiation optically coupled to a radiation guide having a proximal end and a distal end, the radiation guide serving to conduct radiation between the proximal end and the distal end, the proximal end of the radiation guide serving to receive the laser radiation from the source, the distal end comprising a tip and serving to at least partially absorb direct the laser radiation and emit secondary radiation indicative of a temperature of the distal end, means to conduct the secondary radiation from the distal end to the proximal end, a detector optically coupled to the proximal end for receiving the secondary radiation and generating an output signal indicative of a distal tip temperature, and means responsive to the output signal for controlling the source of laser radiation to maintain the output signal at a predetermined level. The tip can be detachable, integral with the distal end, or the distal end itself can be a tip.

The surgical laser is characterized by the wavelength of the laser radiation ranging from about 190 nm to about 11000 nm. The wavelength of the laser radiation also can range from about 400 nm to 2700 nm, or from about 800 nm to about 2100 nm. The radiation guide can comprise an optical fiber, as well as a hollow guide.

The detector is configured to register optical radiation having a wavelength ranging from about 300 nm to about 18000 nm. Also, the detector is configured to register optical radiation having a wavelength ranging from about 1000 nm to 2700 nm. Also, the detector is configured to register the radiation having a wavelength ranging from about 1300 nm to 2700 nm. Also, the detector is configured to register the radiation having a wavelength ranging from about 300 nm to 1100 nm or from about 300 nm to about 1500 nm. Also, the detector is configured to register the radiation having a wavelength ranging from about 1500 nm to about 2700 nm. The predetermined level of the output signal corresponds to a predetermined temperature of the tip.

In the surgical laser device the predetermined temperature of the tip correlates with a predetermined size of a coagulation zone during treatment. The optical fiber can be a bare optical fiber end adapted to at least partially absorb the laser radiation on the distal end to create a thermo optical tip. The radiation guide can comprise an optical or hollow fiber with its proximal end receiving the laser radiation, its distal end being optically connected with the proximal end of the thermo optical tip, which distal end at least partially absorbs the laser radiation. The secondary radiation can be fluorescent radiation. The tip comprises embedded absorption material. The absorption material comprises carbon particles, metal ions, or metal oxides.

The thermo optical tip has absorption in the range of 0.05 to 1, preferably in the range of 0.5 to 1.

The present invention also provides a method of producing a thermo optical tip comprising obtaining an optical tip made of an optical transparent material; contacting an optically absorbing material with the tip; embedding the optically absorbing material onto a surface of the tip or into the material of the tip by applying the laser power to the tip; and annealing the tip by applying the laser power to the tip. Applying the laser power comprises automatically adjusting the laser power to maintain a predetermine temperature level of the tip. The method further comprises cleaning the tip after embedding the optically absorbing material onto a surface of the tip or into the material of the tip mechanically or chemically. The method further comprises cooling the tip after annealing the tip by applying the laser power to the tip and another annealing step after the cooling step.

An embodiment of the surgical laser device of the present invention comprises a source of laser radiation optically coupled to a radiation guide having a proximal end and a distal end and serving to conduct the laser radiation between the proximal end and the distal end; the proximal end serving to receive the laser radiation from the source of laser radiation; the distal end comprising a tip for operating on tissue; and a mechanism for controlling a force applied by the tip to the tissue. The mechanism can be a spring-loaded mechanism. The mechanism further comprises a force or pressure sensor and a controlling system responsive to an output signal from the sensor, the controlling system serving to control the source of laser radiation to maintain a laser power or temperature of the tip at a predetermined level.

Another embodiment of the surgical laser device of the present invention comprises sources of light radiation comprising at least one laser sources optically coupled to a radiation guide having a proximal end and a distal end and being adapted to conduct the laser radiation between the proximal end and the distal end; the proximal end of the radiation guide being adapted to receive the laser radiation from the source; means for conducting reflected and/or backscattered radiation from the distal end to the proximal end; a detector for optically coupling receiving the reflected and/or backscattered radiation and for generating an output signal; and means for adjusting or terminating the laser radiation based on the output signal. The reflected and/or backscattered radiation received from the distal end is a type of radiation different from the laser radiation used for tissue surgery.

Another embodiment of the surgical laser device of the present invention comprises a source of laser radiation optically coupled to a radiation guide having a proximal end and a distal end and being adapted to conduct the laser radiation between the proximal end and the distal end; the proximal end of the radiation guide being adapted to receive the laser radiation from the source of laser radiation; the distal end being adapted to at least partially absorb the laser radiation, to heat up by absorbing the laser radiation, and to emit secondary radiation after being heated up; and the secondary radiation being of sufficient power to cut, coagulation, vaporize or ablate biological tissue. The secondary radiation can be a black body incandescent radiation. The surgical laser device of the present invention further comprises an optical system optically coupled with the distal tip for delivering the secondary radiation to the tissue. The optical system can be a reflector or a lens. The optical system can be a concentrator or a waveguide. The sides of the tip can be adapted for emitting secondary radiation from one or more sides of the tip.

BRIEF DESCRIPTION OF THE DRAWINGS

FIGS. 7a and 7b show density of heat dissipation energy from radiation and heat conduction for a cylinder with diameter 0.4 mm;
FIG. 9 is a schematic illustration of different shapes of a tip.

DETAILED DESRIPTION OF THE PREFERED EMBODIMENTS

The present invention utilizes the concept of controlling the laser power during laser surgery based on optical and other signals from the tip and the tissue. A laser surgical system generally comprises several basic components, such as a laser, a delivery system, a tip and a control system. A tip may be considered as a particular case of a thermo-optical tip (TOT). TOT is an optical and mechanical element which could be used to modify or treat soft and hard tissues, including cutting, coagulation, vaporization, carbonization, and ablation of tissues.

TOT typically works in contact with the treated tissue and provides tissue cutting, coagulation or ablation at least partially due to heat conduction from the tip heated by optical radiation absorbed by the tip. The tissue cutting action with TOT occurs at least partially due to the thermo-mechanical force or ablation. Tissue coagulation with TOT occurs at least partially due to the thermal conduction from the tip to the tissue and due to absorption of secondary radiation emitted from the tip heated to a high temperature by the laser radiation. The secondary radiation can be heat (thermal) radiation or luminescence.

Figure 1:
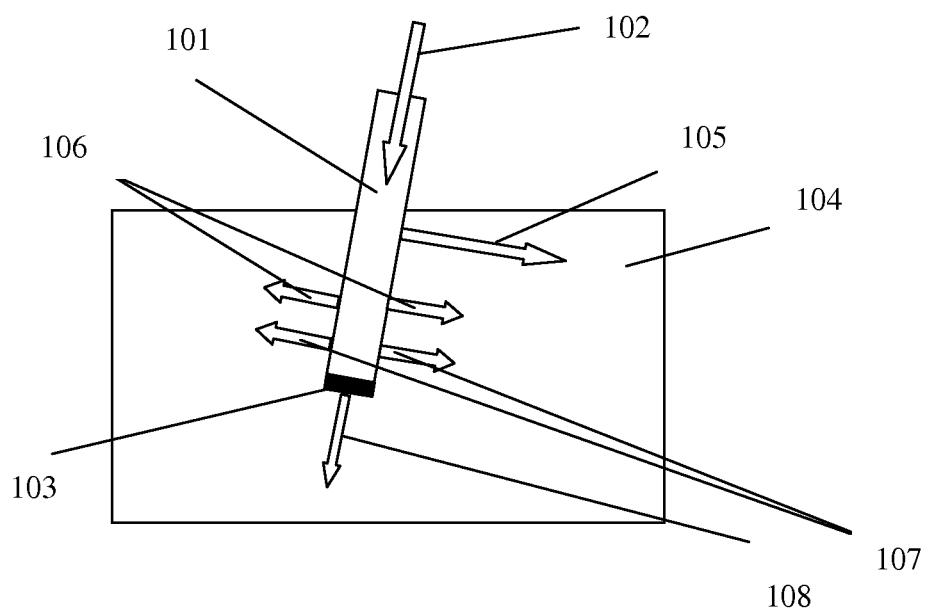
FIG. 1 is a schematic illustration of thermo optical tip.

FIG. 1 provides a schematic illustration of the TOT. An optical element 101 can be, glass, crystal, such as sapphire, ceramic, composite material or another optical material. It can be built from a highly absorbing material, such as a semiconductor, metal or doped optical material. Optical radiation 102 is coupled into the optical element 101. Optical radiation completely or partially is absorbed into an absorbing element 103 which can be a film of material, such as metal, metal oxide, carbon or other material attached to the optical element 101 by means of sintering, bonding or other attachment method. The absorbing element 103 may be located inside the optical element 101. For example, the optical element 101 can be a hollow optical or metal fiber with the absorbing element 103, such as a metal wire in the hole. The optical element 101 can be combined with the absorbing element 103. For example, an optical element from a transparent glass or crystal can be doped by ions which can absorb optical radiation. For quartz or glass fiber different metal ions can be Nd, Cr, Fe, Yt, Er and others. The TOT is comprised of the optical element 101 and the absorbing element 103. The TOT can work in contact with a treated tissue 104. The TOT interacts with the tissue 104 by means of mechanical force 105 in the direction of movement of the tip, by heat diffusion 106, by heat radiation 107 and by residual optical radiation 108.

Figure 2:
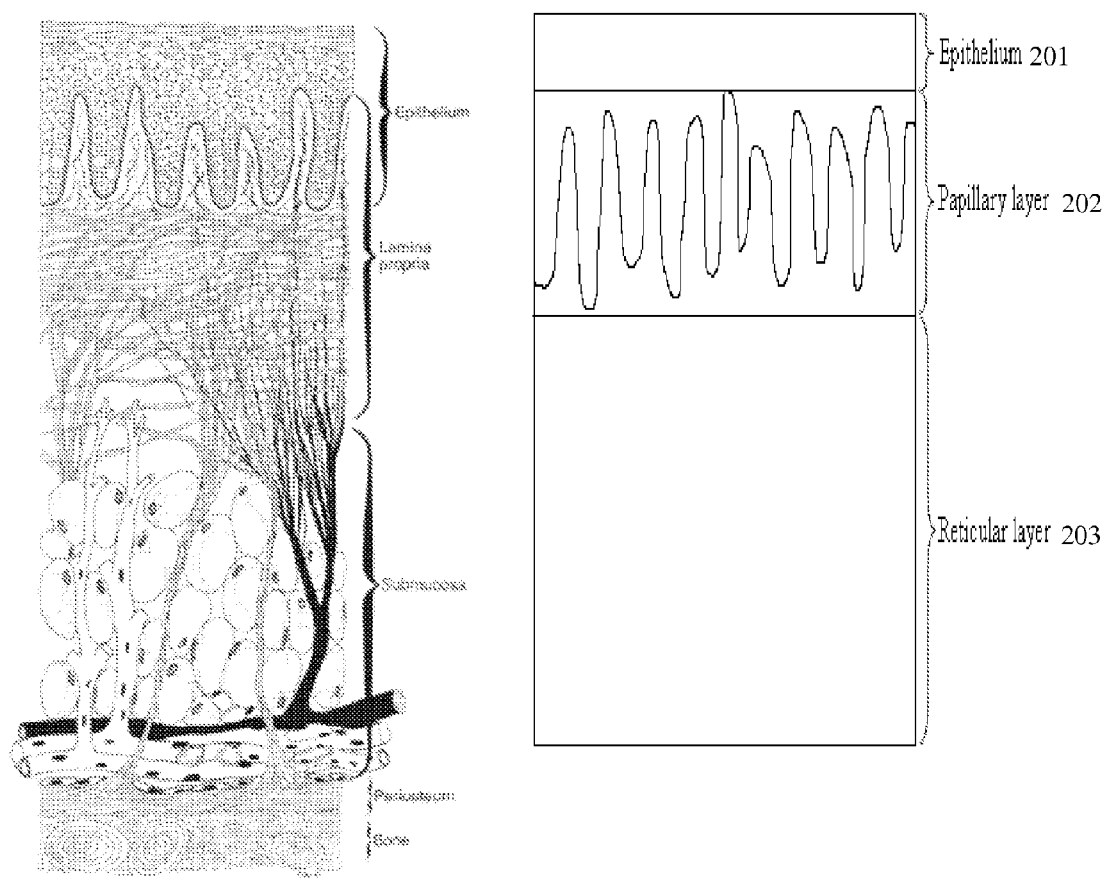
FIG. 2 shows a typical structure of soft oral tissue.

Optical and heat radiation is absorbed by soft tissue (mucosa) due to three basic chromophores: hemoglobin (oxyhemoglobin and deoxyhemoglobin), water and collagen. The typical structure of soft tissue, such as oral mucosa, is shown in FIG. 2. There are three main tissue components of the oral mucosa: the oral epithelium, the underlying connective tissue layer, called the lamina propria, and the submucosa layer. The thickness of the oral epithelium may vary from 50 to 750 μm; for gingival epithelium it is about 200-400 μm. The interface between the oral epithelium and the lamina propria is usually irregularly-shaped, and called basement membrane. The thickness of the gingival mucosa oral epithelium, including the epithelial papillae, ranges from 200 to 300 μm. The thickness of the gingival mucosa lamina propria is approximately the same. The lamina propria may be divided into two layers: the superficial papillary layer (associated with the epithelial papillae) and the deeper reticular layer. In the papillary layer, collagen fibers are thin and loosely arranged, and many capillary loops are present. The reticular layer has collagen fibers arranged in thick bundles that tend to lie parallel to the surface plane.

For tissue treatment, it is necessary to choose optimal laser parameters such as wavelength, pulsewidth and power density. The layers described above have different optical properties because of their different structure and components. The absorption coefficient of each layer depends on the content of the base chromophores in that layer—water, blood and collagen. The absorption coefficient of epithelium can be calculated based on the knowledge of water content in epithelium using the following formula:

$$\mu_{ae} = f_w \mu_{aw},$$

where $f_w$—water content in the epithelium, $\mu_{aw}$—water absorption coefficient, $\mu_{aw}$—oral epithelium absorption coefficient.

The absorption coefficients of papillary and reticular layers can be calculated on the basis of knowledge of the blood, water and collagen content in these layers using the following formula:

$$\mu_{ai} = f_{wi}\mu_{aw} + f_{bi}\mu_{ab} + f_{ci}\mu_{ac},$$

where $f_{wi}$, $f_{bi}$ and $f_{ci}$—water, blood and collagen content in a considered layer, $\mu_{ab}$—whole blood absorption coefficient (45% hematocrit, 75% oxygen saturation), $\mu_{ac}$—collagen absorption coefficient, $\mu_{ai}$—absorption coefficient of a considered layer.

Figure 3A:
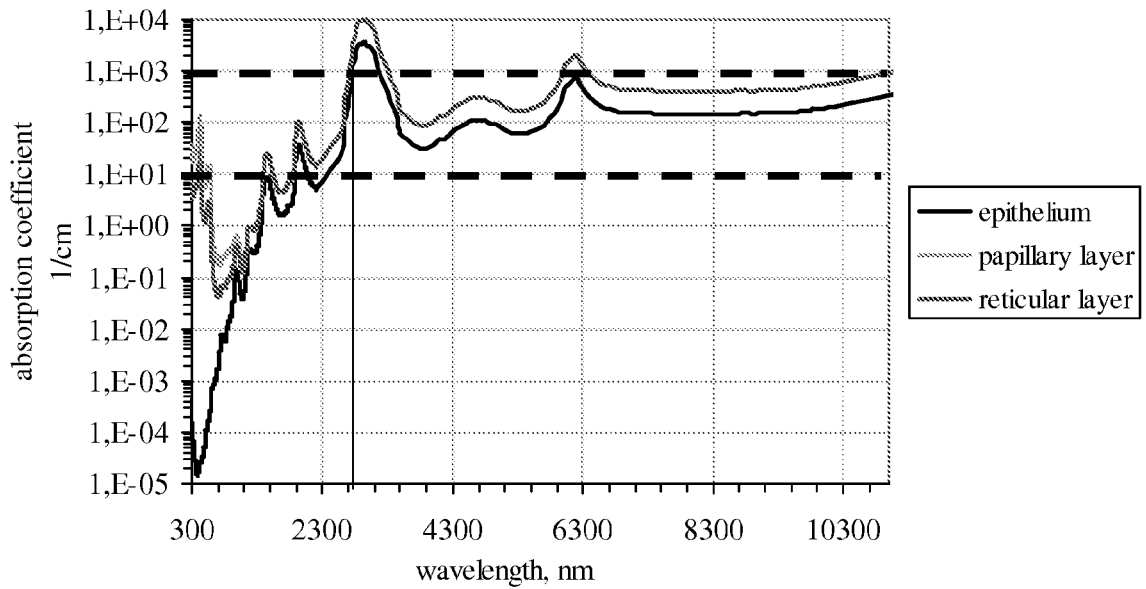
FIGS. 3a and 3b show absorption spectra for soft tissue layers.
Figure 3B:
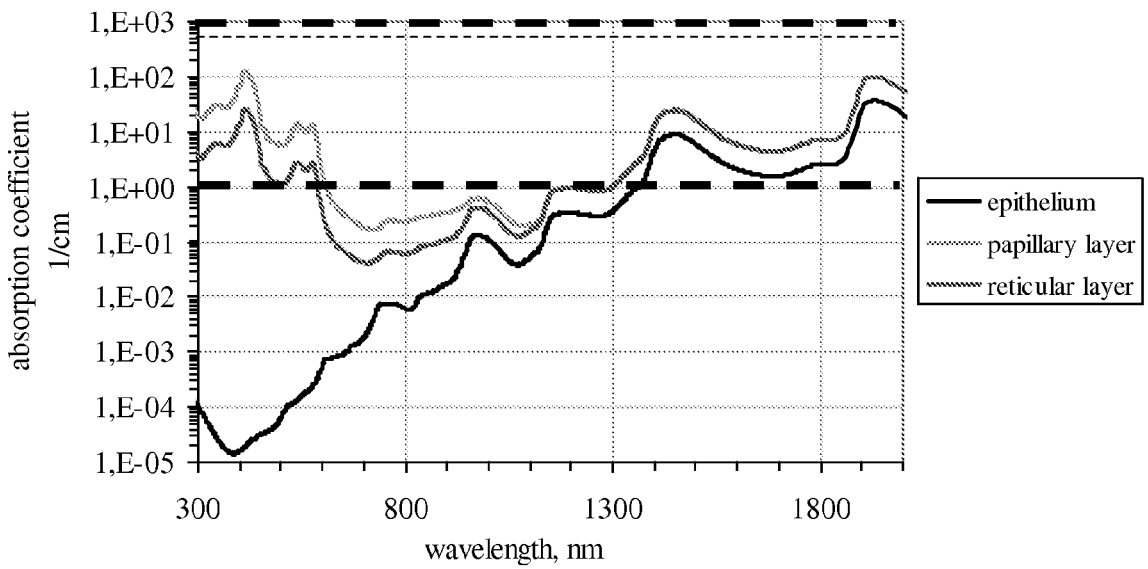

Absorption spectra for the papillary and reticular layers are illustrated in FIG. 3. For the papillary layer it is considered that the blood volume content equals about 5%, water volume content equals about 75%, and that the remaining volume of about 20% is occupied by biopolymers such as collagen. For the reticular layer it is considered that the blood volume content equals about 1%, the water volume content equals about 75%, and biopolymer content equals about 24%.

For optimum optical coagulation and cutting with optical radiation (including laser) or heat, radiation should be absorbed in the layer of tissue surrounding the tip at a depth $z_a$ ranging from about 0.001 to about 0.1 cm. It corresponds to the coefficient of absorption $\mu_a$ in the range of about 10-1000 cm$^{-1}$ in accordance with the following formula:

$$\mu_\alpha \approx 1/z_\alpha$$

It follows from FIG. 3 that the wavelength λ which satisfies this condition is: for epithelium λ>about 1300 nm, for papillary layer λ<about 600 nm and λ>about 1100 nm, for the reticular and papillary layers λ<about 600 nm and λ>about 1100 nm. Therefore, for direct optical cutting and coagulation, the optimal laser wavelength should be selected from these ranges. As it was mentioned before, the most popular dental surgical lasers operate in the spectral region where direct optical absorption of the laser radiation is much lower and, therefore, the thermo-optical tip is instrumental in the tissue cutting and coagulation process. There are two major mechanisms of a heat transfer from the TOT to the tissue. One is thermal conduction, the other one is thermal radiation from a tip (also known as a black body radiation in case if the tip can be considered as "black", e.g. absorbing substantially 100% of radiation at all wavelengths in the visible and infrared range within the thermal radiation spectrum, see FIG. 4). We will refer to that secondary radiation from the tip as heat radiation or incandensent radiation.

Figure 4:
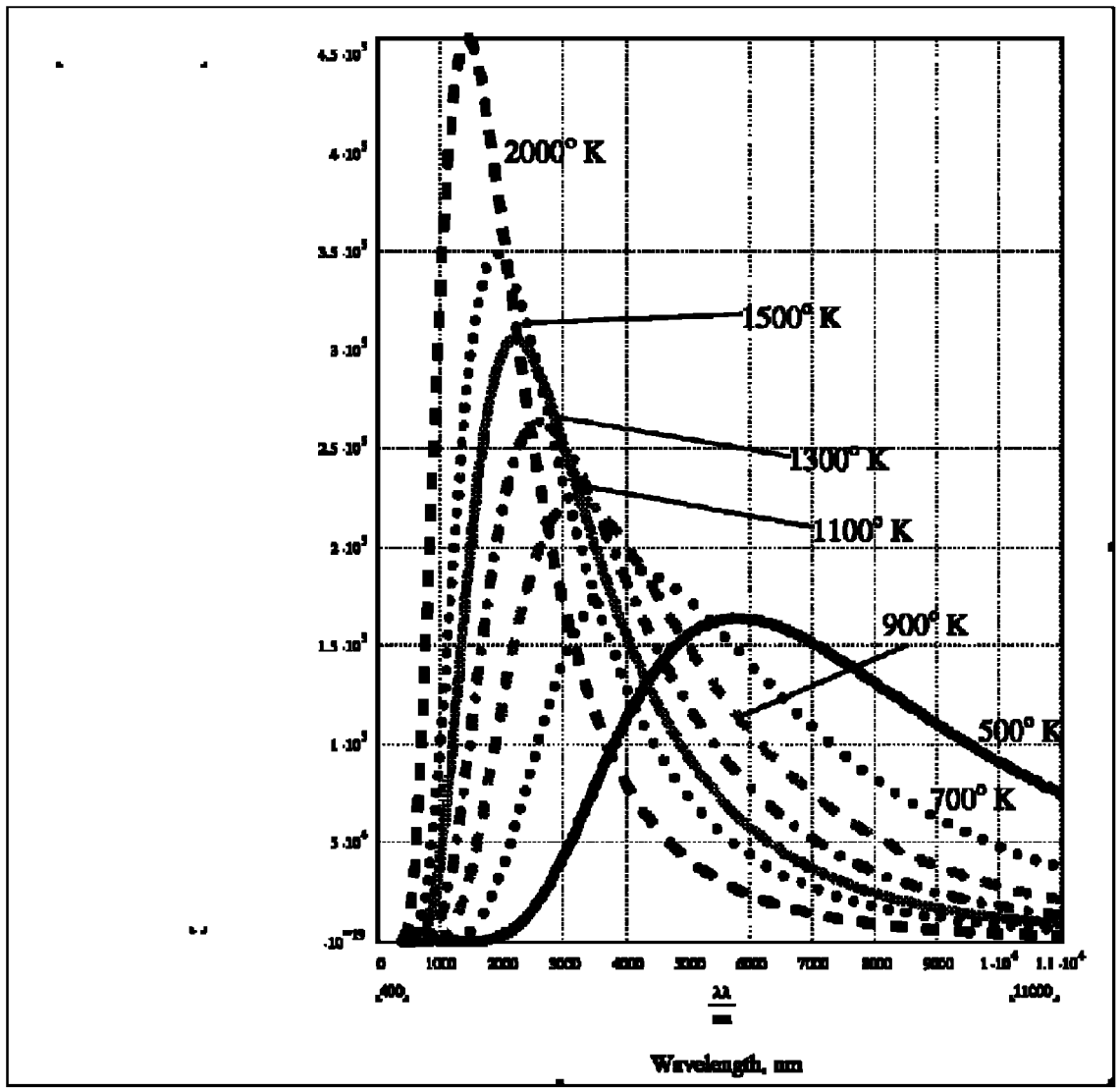
FIG. 4 shows black body thermal radiation spectra for different temperatures.
Figure 5:
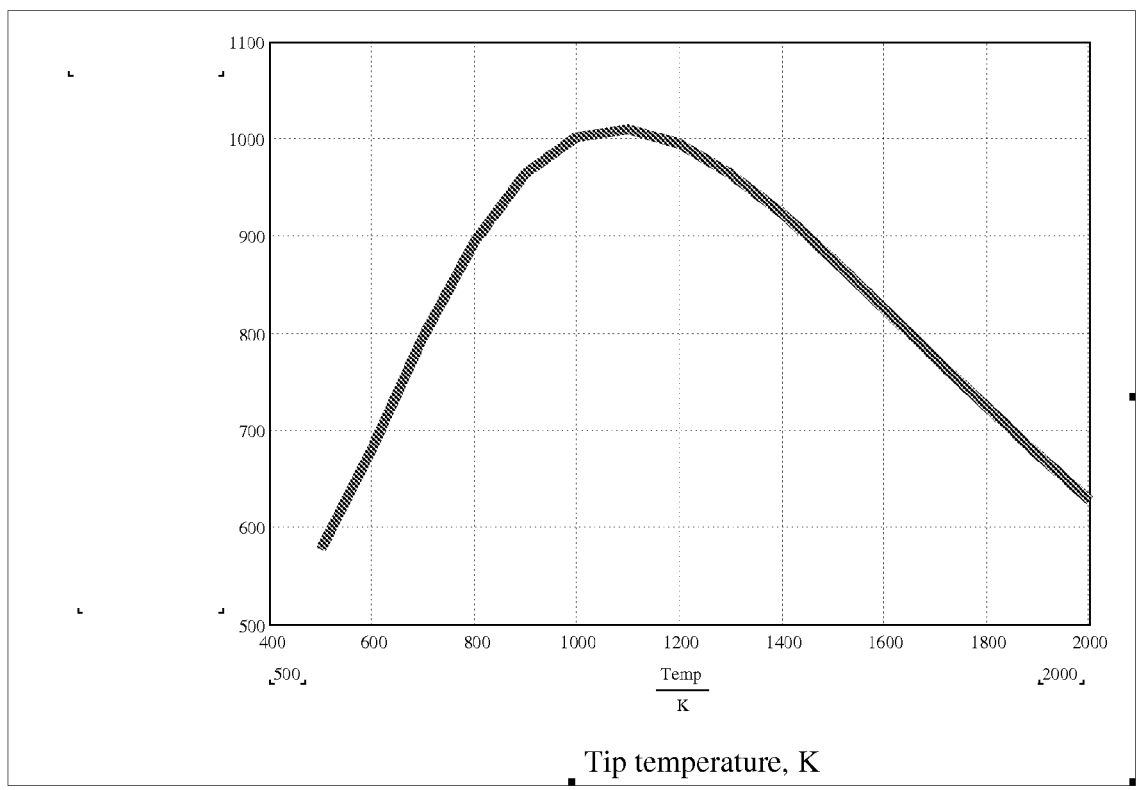
FIG. 5 shows effective absorption in tissue as function of tip temperature.

The heat radiation emitted by the TOT can be absorbed by the tissue, as well as by direct laser radiation. However, heat radiation has a very broad spectrum of wavelengths, and the position of the power maximum in this broad spectrum is defined by the temperature of the tip, as shown in FIG. 4. The effect of heat radiation energy on tissue can be defined based on the average (effective) coefficient $\mu_{aeff}$ of absorption of the tissue and can be estimated based on a cross-section integral of tissue absorption spectrum (FIGS. 3a and 3b) and heat radiation spectrum (FIG. 4). FIG. 5 shows $\mu_{aeff}$ as function of tip temperature. TOT produces coagulation and cutting effect primarily by heat diffusion and absorbtiption of heat and laser radiations.

Figure 6:
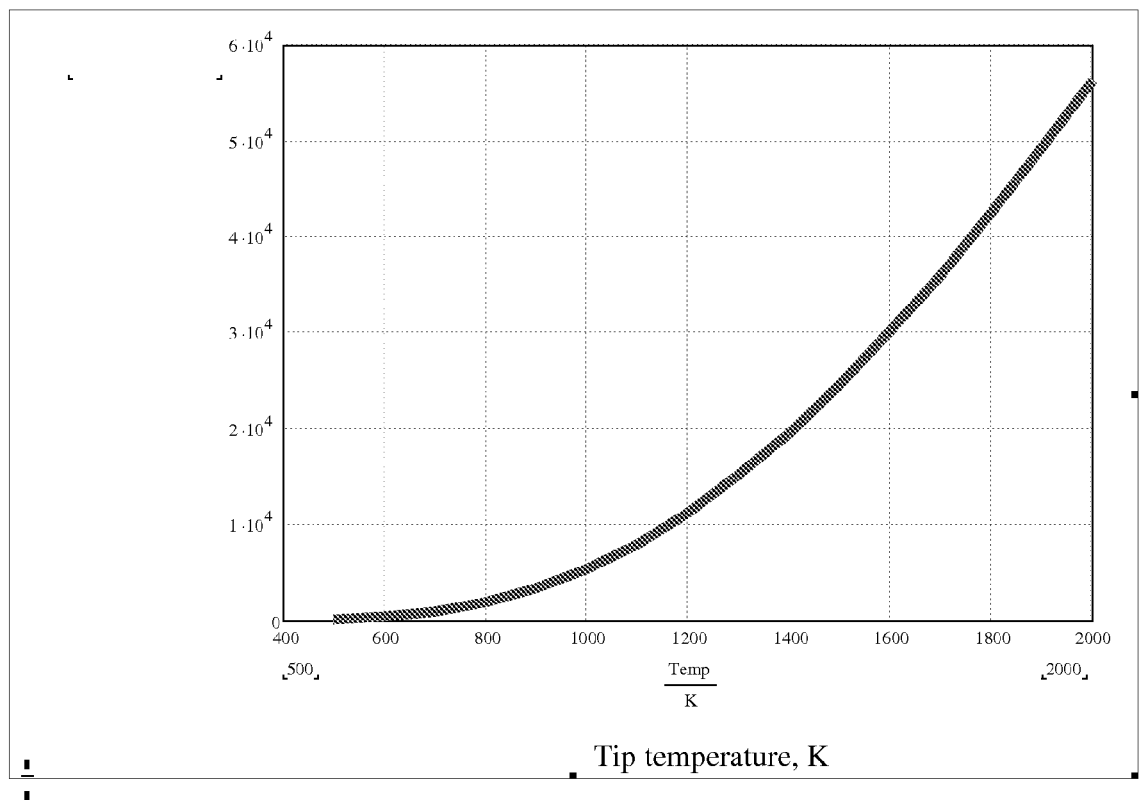
FIG. 6 shows total power of incandescent tip radiation as function of tip temperature.

As one can see in FIG. 5, an effective coefficient of absorption of mucosa $\mu_{aeff}$ in the range of the tip temperatures from about 500° K to about 2000° K varies from about 600 to about 1000 cm$^{-1}$, which corresponds to the depth of penetration in the tissue from about 10 to about 15 μm. Such penetration is typical for the 10600 nm CO$_2$ laser wavelength. The CO$_2$ laser is considered as one of the best lasers for soft tissue surgery with optimum hemostasis. That laser provides minimal necessary hemostasis, short healing time and minimal post-operative complication. TOT can emit heat radiation penetration and provide a coagulation zone similar to those of a CO$_2$ laser. The power of heat radiation increases with an increase in temperature of TOT, as shown in FIG. 6. TOT works as a spectral converter of light radiation from wavelengths with low absorption in tissue to wavelengths with very high absorption (pumping radiation), providing a much stronger effect on the tissue than pumping radiation. The efficiency of TOT as a spectrum converter increases with temperature (FIG. 6). The optimum temperature of TOT for best absorption is from around 500 to about 2000° K. Due to the efficiency of conversion, the optimum temperature can be in the range from about 900° K to about 4000° K. Incidence radiation of TOT has substantially isotropic distribution and can be directed and concentrated in a preferable direction by using mirrors, lenses, optical condensers and waveguides.

The tissue surrounding the TOT is heated simultaneously by heat conduction and by secondary radiation. It was found that for the TOT arrangement both mechanisms can be very comparable. FIGS. 7a and 7b show the density of heat dissipation of energy from radiation and heat conduction of a cylinder with a diameter of about 0.4 mm. The cylinder is moved into the tissue with speeds of 1 mm/s (FIGS. 7a) and 10 mm/s (FIG. 7b), respectively. For high-speed cutting of tissues of as much as 10 mm/s, the heat radiation coagulation mechanism starts to dominate over the heat conduction mechanism for a temperature of about 1000° K and higher. For the low speed of cutting of oral tissues of 1 mm/s, the heat radiation coagulation mechanism starts to dominate over the heat conduction mechanism for a temperature of about 1700° K and higher. The temperature of TOT can be in the range of 500-12000° K, preferably in the range of 800-1500° K for contact cutting, coagulation and ablation and in the range of 1200-3500° K for non-contact cutting, coagulation and ablation.

TOT can be used in a non-contact or quasi-contact mode (by touching treated tissue with little pressure). Heat radiation can coagulate and ablate the tissue due to the absorption of heat radiation by water contained in the tissue. Since for the temperature of TOT in the range of about 500-2000° K the coefficient of water absorption is in the range of 600-1000 $cm^{-1}$, the net effect on tissue using a non-contact tip can be similar to the effect of a $CO_2$ laser on the tissue in a non-contact mode.

Figure 8:
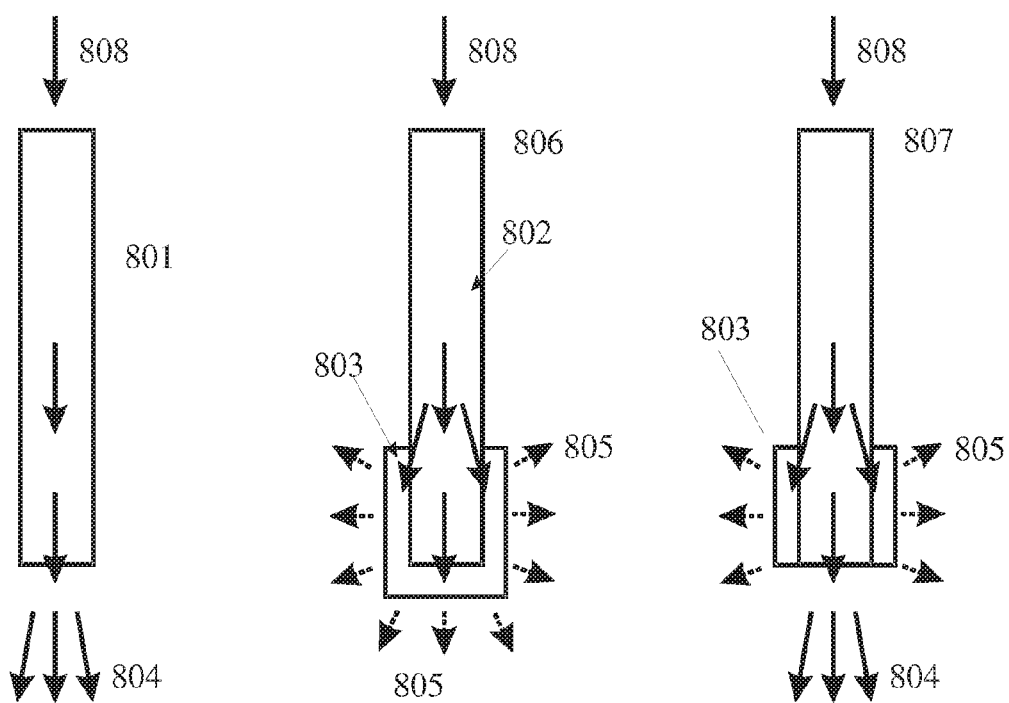
FIG. 8 is a schematic illustration of optical and TOT with different absorption distribution.

FIG. 8 illustrates optical tip 801 and thermo-optical tips 806 and 807 that can be used for tissue operation. These tips differ by presence (absence) and localization of laser light absorptive part at the output edge. The absorptive part 803 of the tip may be located inside the transparent part 802, surround it or be located outside of the transparent part and leaving a possibility for the light 808 to pass through completely or partially, as shown in FIG. 8. In any case, some residual laser light 804 is coming out of the tip, and secondary heat radiation 805 is coming from the absorbing light and heated to high-temperature part of the tip.

In present invention, an optimum embodiment of a TOT operation was discovered. In one preferred embodiment, the tissue cutting effect is produced by means of a thermo mechanical cut. Thermo mechanical cut occurs from cutting by the mechanical force from the sharp edge of TOT. As illustrated in FIG. 9, TOT may have different shapes, such as a cone 901, cylinder 903, wedge 905, or knife 907. The material of such tips can be, for example, glass, quarts, and optical crystal and ceramic. Each tip can comprise an absorber 902, 904, 906 or 908 located on the part of the TOT surface irradiated by light. A preferable location of absorber is at the sharpest part of the TOT, which is used for thermal-mechanical cut. The absorber can be made of carbon, metal or their alloy and compositions, and thermally or chemically adhered to the transparent part of the TOT, or sintered to the TOT. The light absorber can be localized inside transparent material. In another embodiment, the TOT can be made of a photonic crystal fiber. In yet another embodiment, tip 910 is made from a wedge-shaped plate of sapphire, which couples light, propagated from optical fiber 909, to the tissue through side 911. In yet another embodiment, the TOT can be made of a transparent material doped by absorbing particles or ions. For example, glass or yyttrium aluminum garnet doped by ions of neodymium ions can be used as material for such type of TOT. A laser with a wavelength of 808 nm can be used for pumping of such TOT. In addition to heat radiation, luminescence emission conversion of laser radiation from the tip at wavelengths of about 1060, 1320 and 1440 nm can be used for tissue treatment and coagulation.

Figure 10:
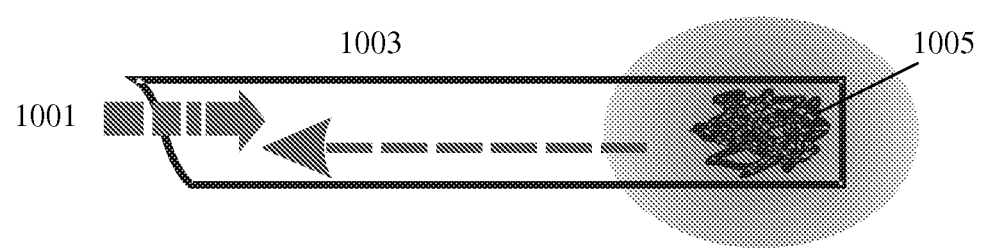
FIG. 10 is a schematic illustration of alternative embodiment of TOT with absorptive powder.

Another example of TOT is shown in FIG. 10. Absorptive particles (powder) of graphite or other material is placed inside quartz tube 1003. Then the edge of the tube is melted using the flame, laser or other heater at temperatures above 1600° C. During this procedure the hollow quartz sphere containing the particles 1005 appears. The inner space of the sphere is connected with the hollow space of the quartz tube. The quartz fiber 1001 is inserted into the distal edge of the tube. Laser radiation propagates along the tube and then directly or reflecting from the tube walls reaches the powder. Laser radiation heats the particles. The particles emits in the infra-red (IR) range and heats the tube walls. IR radiation and heated walls of the tip interact with soft tissue and produce coagulation, evaporation, carbonization and ablation. It should be noticed that the tip may be designed in such a way that the laser radiation passes partially through the absorptive part. The transmission can be in the range from 0 to about 95%. The TOT can be made of a material with high absorption. For example, TOT can be made of a short piece of tube from highly absorbing material.

Since the secondary radiation from the distal tip propagates in all directions, its delivery to the tissue to perform treatment can be improved. Normally, some part of that radiation propagates forward and can be used directly to treat tissue. Another part of that radiation propagates backward to the optical fiber or TOT and then produces heat in the fiber tip or TOT and also leaks to the side of the fiber or TOT, which could be used for side cutting or coagulation. The fiber tip or TOT for this embodiment can be made from quarts fiber or a material with a high refractive index, such as sapphire, to enhance the effect of backward light propagation. An additional optical system can collect this heat radiation and redirect/concentrate it onto the tissue. FIG. 11a shows one embodiment of such redirection using a minor 1105. Mirror 1105 can be made of several plane segments, or it can have a conical, spherical, parabolic or elliptical shape. The light 1101 enters the transparent part of the tip 1102, heats up absorbing part 1003, which emits the secondary radiation. One portion of radiation 1007 partially propagates back to the fiber. Another portion 1006 propagates forward to the tissue 1004. Yet another portion 1008 propagates sideways, reflects from mirror 1005 and gets redirected to the tissue 1004. FIG. 11b shows an alternative configuration for such minor. The tip with optical concentration of incandescence radiation can be used for non-contact tissue cutting, coagulation, vaporization, ablation and heating similar to $CO_2$ or Erbium lasers in non-contact mode of treatment. The cost of such a device with semiconductor GaAs lasers used for pumping TOT is significantly lower than that of the typical mid- and far infra-red lasers.

Figure 12:
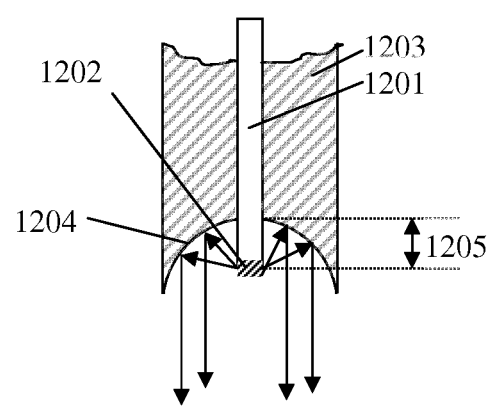
FIG. 12 is a schematic illustration of non-contact or quasi-contact TOT.

FIG. 12 shows another embodiment with a noncontact or quasi contact tip. TOT tip 1201 with a diameter of about 0.1-0.5 mm and an absorbing element 1202 is mounted inside the tube 1203 with high reflective surface 1204. Spherical or elliptical surface 1204 is polished and has a high coefficient of reflection on IR wavelength range due to, for example, gold coating. The distal end of the tip with an absorbing element is positioned relative to the center of surface 1204 to provide the desired diameter of IR radiation beam from TOT. For example, if distance 1205 is a half of the curvature radius of surface 1204, the IR beam is quasi collimated with the diameter close to the outer diameter of the tube. The IR beam can be focused on the tissue if distance 1205 is between 0 and a half of the curvature radius of surface 1204.

It is very important to monitor and control the tip temperature during the surgery to obtain consistent and predictable results, because the TOT temperature has more direct impact on the tissue as compared to light power. In case of simple heat conduction in a linear media without modification and phase transition, the temperature of TOT $T_{TOT}$ would be a simple function of the coefficient of light absorption k in the tip and laser power $P_L$ as described by the following formula:

$$T_{TOT} \sim k \cdot P_L$$

However, taking into account an additional mechanism of heat transfer via secondary radiation, as well as nonlinear tissue modification, changing the cutting speed and the level of optical and thermal coupling between the tip and the tissue, it is difficult and impractical to maintain the tip temperature without some feedback mechanism.

Such a feedback can be based on optical (infrared and visible) emission from a hot tip. The spectrum varies depending on the temperature, as shown in FIG. 4, and it can be seen that a substantial part of the emission spectrum overlaps with the transmission spectrum of a fiber optic light guide delivery system. Even with a quartz fiber, especially quartz fiber with a low concentration of OH, transmission goes to about 2.7 µm and, therefore, a substantial part of the secondary emission can propagate back to the proximal end of the fiber and be detected by a photo detector.

For even further increased sensitivity, a special infrared fiber and a hollow fiber can be used. If such sensitivity is sufficient, then the spectral range for registration may be limited to <2.2 µm spectral range, where a silica fiber with low OH is highly transparent and the signal level will not depend on the length of the fiber.

Alternatively, the fiber length can be measured using known optoelectronic means, such as interferometry, the time of flight, phase modulation and other known methods. Then calibration of a thermal radiation feedback signal can be adjusted for the fiber length. In the present invention we discovered that a partially absorbing laser radiation TOT emits enough optical power to be detected and used to control measure and maintain the TOT's temperature and, therefore, maximally avoid tissue unwonted damage as pyrolysis and carbonization and the tip degradation. Also, the tip's temperature can be maintained in a broad range, from 300 to 1500° C. for quartz fiber and 300 to 2000° C. for sapphire tip, not only to avoid tip destruction or degradation, but also to provide consistent tissue cutting with desired speed and level of coagulation or collateral thermal damage. Several embodiments of technical realizations of a feedback mechanism based on TOT's secondary radiation are described below.

For a high-temperature tip with $T_{TOT}$ in the range of 1500-4000° C., thermal radiation can be measured in the range of 0.6-2.7 µm, preferably 1.0-2.7 µm or 1.3-2.7 µm or 2.2-2.7 µm. These ranges of wavelengths can be delivered through a silica fiber. For medium temperature tip with $T_{TOT}$ in the range 300-1500° C., thermal radiation can be measured in the range of 1.0-2.7 µm preferablly 1.3-2.7 µm or 2.2-2.7 µm. These ranges of wavelengths can be delivered using silica fiber. For lower temperature tip with $T_{TOT}$ in the range of 100-300° C., thermal radiation can be measured in the range of 1.3-18 µm, preferably 2.2-2.7 µm or 2.2-18 µm. These preferable wavelengths can be delivered using IR fiber such as glass: heavy metal fluoride (ZBLAN—(ZrF4-BaF2-LaF3-AlF3-NaF)), germanate (GeO2-PbO), chalcogenide (As2S3 and AsGeTeSe), single crystal (sapphire), crystal polycrystalline (AgBrCl) and hollow waveguide from metal, glass or crystal For measuring of $T_{TOT}$ one can use a signal integrated over spectral ranges described above. Absolute value of $T_{TOT}$ can be defined by calibration of a thermal channel by heat radiation sources. For example, a distal end of a fiber can be placed in a close vicinity to or in contact with an object heated by electricity or flame and signal can be measured at multiple set points. Simultaneously, absolute temperature is measured using traditional means such as IR thermometer, thermocouple or other thermal sensor. Such procedure results in calibration of thermal optoelectronic signal to a real tip temperature. It should be noted that the temperature distribution within the tip and fiber can be inhomogeneous, therefore, some effective temperature can be measured and calibrated. In another embodiment, simultaneous measurement of heat radiation in two or more wavelength ranges can be performed, for example one channel 300 nm to 1100 nm or 300 nm to 1500 nm and another channel 1500 nm to 2700 nm. In this case, $T_{TOT}$ can be defined based on the ratio of readings in these two channels, rather than an absolute signal value in a single channel.

During laser cutting, the speed of cutting v can be changed by the operator in a certain range, typically 0.5-50 mm/s. Thus, several modes of $T_{TOT}$ level are proposed:

$T_{TOT}=T_0$ for $v_{min}<v<v_{max}$, and $T_{TOP}=T_{min}$ $v<v_{min}$. $T_0=500\div3000°$ K, preferably $T_0=500\div1100K$. Tmin=300÷400° K.

$T_{TOT}=T_0+q\cdot(v-v_{min})^n$, q is a coefficient, n=0.2-10 and $T_{TOP}=T_{min}$, if v<vmin.

For constant coagulation zone around the cut, which is independent of speed v, parameter n can be about 0.5-2. To maintain approximately constant coagulation of treated tissue $T_{TOT}$ level has to be decreased when speed of cutting is decreases. Speed of cutting can be measured independently by mechanical, optical, electrical or magnetic sensor. $T_{TOT}$ can be regulated based on other signals from treatment zone such as resistance force between tip and the tissue. For example, the force can be increased due to cutting high fibrotic tissue fragment and $T_{TOT}$ can be increased for easier and smoother cutting. In another embodiment, optical or acoustical signal related to changes in scattering or absorption in the treatment tissue can be used for control of $T_{TOT}$ to achieve a consistent effect on the tissue.

The combination of TOT with predetermined absorption k and a real-time temperature control provides consistent $T_{TOT}$ as described above and easy, minimally invasive cutting with optimum hemostasis in a broad range of moving speed. Laser power is adjusted in real time to maintain predetermined temperature of the tip. Such automatic power control (APC) mode provides smooth and minimally invasive laser treatment. A method and apparatus for real-time control of temperature of the tip or tissue in contact with the tip is described below.

In another embodiment measured $T_{TOT}$ level can be presented to an user by visual or audio signals in real time. The user can adjust power or speed of treatment based on this signals to maintain desire treatment goal.

The temperature of the output edge of the tip depends on the absorbed laser power. The absorbed power depends on incident power and the effective absorption of a working edge of the tip. The absorption depends on the concentration and amount of absorptive centers. TOT preparation is a procedure which is aimed at the creation of tip-to-tip reproducible amount of absorptive centers in the volume or at the surface of the tip's working edge. In one embodiment, we propose to arrange preparation in several stages under the control of TOT temperature (see FIG. 11). For preparation, laser energy delivered in TOT can be used. Control means laser energy variation in dependence on intensity of thermal radiation in 1-2.7 µm, preferably in 1.3-2.5 µm, appears due to TOT 111 heating under the influence of laser radiation.

Figure 11:
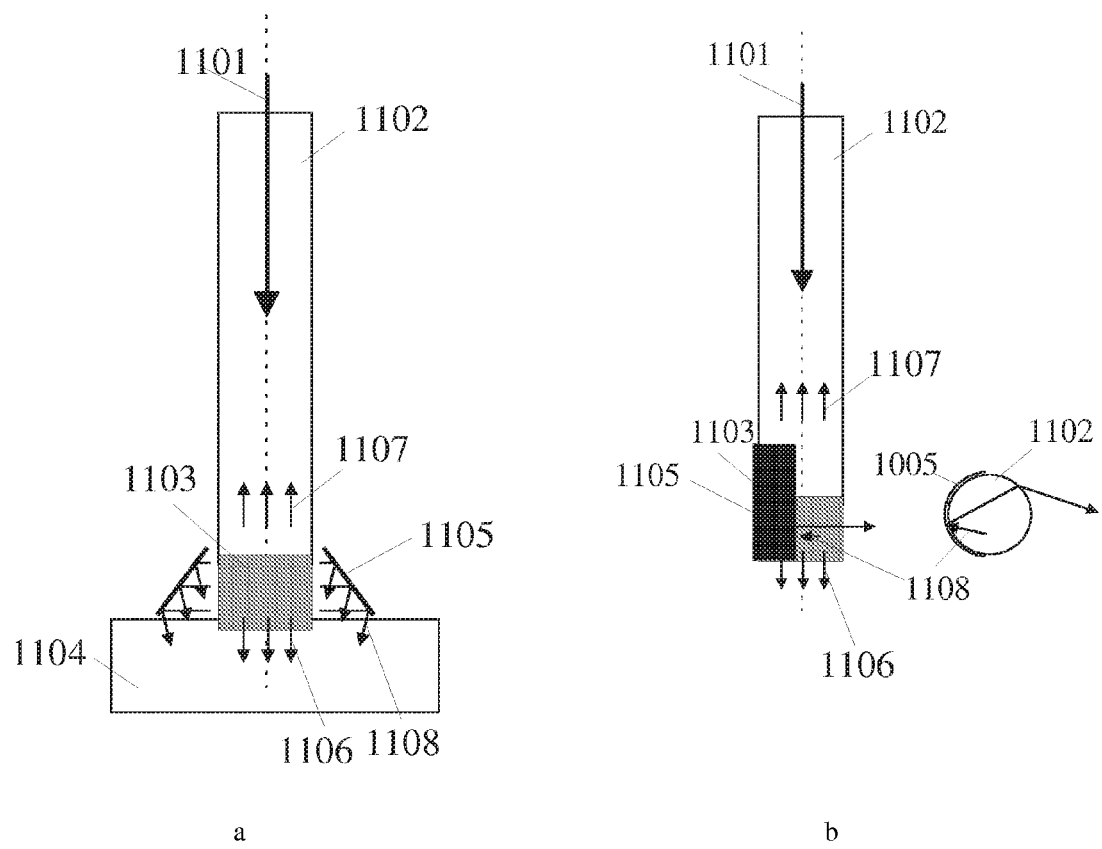
FIGS. 11a and 11b are a schematic illustration of tip with optical system for better delivery of incandescent radiation.

The 1$^{st}$ stage of preparation ("burn-in procedure") is illustrated in 117, 119, and 121 in FIG. 11. The purpose of this stage is to create the absorptive centers on the surface of TOT and embed them into its volume. At this stage, the distal edge of TOT made of glass, quartz or optical crystal 111 is put in contact (with some pressure) with absorptive medium comprised of the absorptive centers 113. Under the influence of laser radiation, the medium is heated up to the temperature of softening or melting of glass or quartz TOT or close to the temperature of melting TOT made of optical crystal. It is desirable that absorptive centers are lightly connected with each other to prevent the waste of laser energy for decomposition. The media 113 may be made of powders or pressed carbon particals including nanoparticles, organic compound, metal, metal oxides and others.

The heated absorptive centers stick to the surface of softened tip material, create bonding between tip absorbing centers, and working edge of the tip plunges inside absorptive medium. The depth of immersion defines the length of tip region having the increased absorption (painting region). The temperature and temperature application time are a very important parameter because it should be high enough for material softening only, but not enough for its melting and evaporation. That is why the temperature should be controlled. For example, for quartz the temperature should be controlled so that it is the range of 1000-1700° C., preferable 1000-1200° C. The control is realized by a close loop control which decreases the laser power when thermal radiation intensity exceeds target level and increases it when the thermal radiation is below the target. The duration of the $1^{st}$ stage of initiation may be between 0.1 and 10 sec.

The $2^{nd}$ stage of preparation involves cleaning. The purpose of the $2^{nd}$ stage is to remove insufficiently integrated absorptive centers from the tip. Cleaning is performed mechanically or chemical without action of laser radiation using a tissue or brush, possibly with cleaning compound, for example alcohol or acid. Cleaning can be performed by high pressure gas or liquid. Second stage can be eliminated by precise control of initial thickness of absorbing material 113, which excludes accumulation of excessive material on the tip. The $2^{nd}$ stage of preparation can be avoided, for example, by precise control of amount of absorbing centers attached to the tip.

The $3^{rd}$ stage of preparation involves annealing of absorptive centers and is illustrated in 124 in FIG. 11. The absorptive centers introduced into the tip's surface or volume may have different dimensions. They may also be surrounded with empty space (pores), which may stimulate the burning of absorptive center in the field of laser radiation. The dimensions of these pores may also be quite different. The absorptive centers surrounded with large pores will be burned out more easily than the centers surrounded with smaller pores. Non-uniform tip heating caused by fluctuations of the dimensions of absorptive centers and porous may considerably decrease its lifetime. Thus, the purpose of the $3^{rd}$ stage is homogenization of the dimensions of absorptive centers. Another goal of the $3^{rd}$ stage can be an improvement in adhesion between absorber and the material of the TOT, thermal inducement of diffusion of absorber and sintering between the absorber and the material of the TOT, and relaxation of mechanical stress in the TOT.

One mechanism of homogenization takes place due to burning out of centers having maximum limit of size because large centers have high absorption cross section and therefore absorb more laser energy than small ones. Thus, the laser power should be high enough for burning out of large centers and not enough for burning out of small ones. During this stage, laser radiation can be applied to the tip which is located in free position in the air.

It is also beneficial to use optical feedback mechanism during first and third stages of the tip initiation to maintain tip temperature at the optimal level. Definitely, optimal level of the temperature is different for the burn-in stage and for the annealing stage. For example, for the $1^{st}$ stage, optimum temperature can be in the range of 1000-2000° C. and for the $3^{rd}$ stage it can be in the range of 600-1000° C.

This process takes place under the TOT temperature control. The level of thermal radiation critical for annealing is lower than the level of thermal radiation critical for "blackening". While the number of large centers decreases, it is necessary to apply more laser power to maintain the level of thermal radiation critical for annealing. If the tip is made of a quartz fiber having a diameter of 400 μm, then the duration of the $3^{rd}$ stage of initiation may be about 0.1-50 s and consist of one to 50 cycles.

Figure 13:
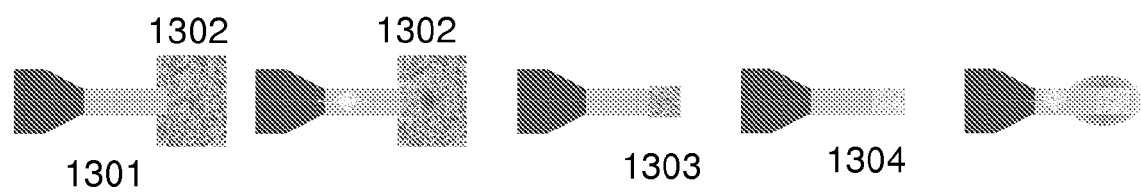
FIG. 13 is a schematic illustration of TOT initiation process.

The initiation process is illustrated in FIG. 13. A clean tip 1301 is brought in contact with initiation agent 1302. Then laser power is applied and initiation agent is burned into or melted into the tip end. After this the tip is removed from the initiation substance and cleaned, it becomes an unfinished tip 1303. Then the tip is annealed at predetermined temperature in several cycles and becomes a finished initiated tip 1304. Then the initiated tip can be applied for contact or non-contact surgery.

Figure 14:
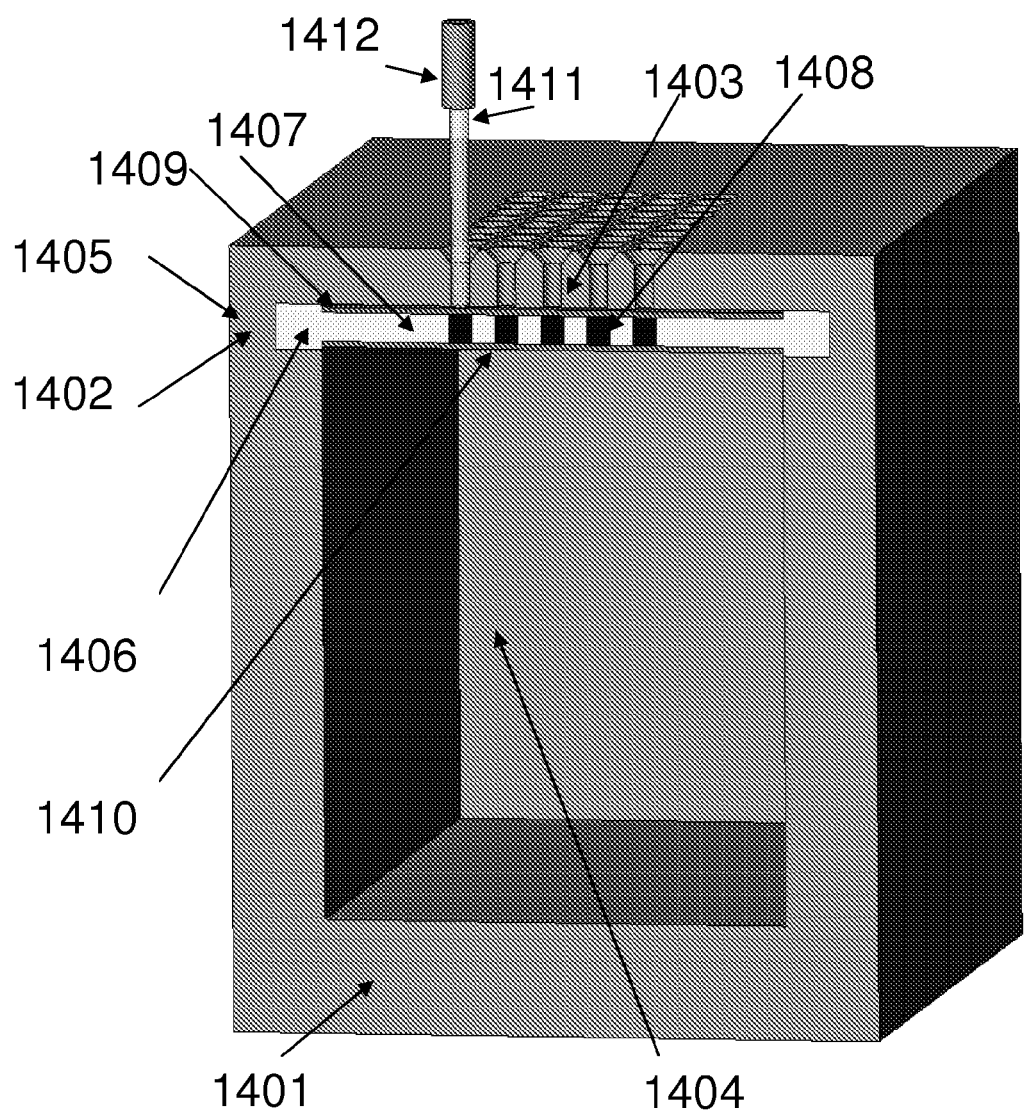
FIG. 14 is a schematic illustration of initiation fixture.

For the initiation one can use a device, represented by FIG. 14. The device allows performing tip initiation for every procedure using individual cell with initiation agent. The device consists of a body 1401 and cartridge 1402. The housing has at least one hole 1403. The housing 1401 has an inner cavity 1404 and 1405 for guiding the cartridge 1402. The cartridge 1402 has a body 1406 which creates space 1407 containing the initializing agent 1408 placed between the strips 1409 and 1410. Holes 1403 and 1407 are coaxial in space. Cartridge 1402 may be replaceable. Initiating substance 1408 can be made in the form of liquid or solid. The substance may be a solution, suspension, powder or granules. Initializing substance may be homogeneous or heterogeneous. Initializing substance 1408 can be carbon particles, allotropic form of carbon, coal, contain by-products of wood, metal, metal oxide and etc. Strips 1409 and 1410 may be made of plastic or paper. Stripes can be painted on the outside or have impregnated by initiation substance 1408.

The initiation fixture operates as follows. Cartridge 1402 with initiation agent 1408 is placed between the strips 1409 and 1410 installed in the guide 1405 of the housing 1401, with the axis of the space 1407 coaxial with the axes of the holes 1403. The optical attachment 1411 of the laser tip 1412 is placed in the opening 1403 so it rests on a strip 1409 with some minimum force. The initiation process starts with the first phase. Through a tip 1411 laser radiation is delivered, resulting in thermal destruction of the strip 1409 and the material of the tip 1411 interacts with initiation agent 1408. In this case, the substance 1408 is embedded in the material of the optical attachment 1411. After burning of substance 1408 the tip 1411 penetrates into the space 1407 and destroys the strip 1410. The tip 1411 penetrates into the cavity 1404 of the housing 1401. Then the second phase of the initialization process starts. Annealing is performed in the cavity 1404. At the end of the annealing laser radiation stops and the initiated tip extracted from the fixture.

Absorbing centers can be encapsulated once, using a special tip initiation fixture. It can be a tube with an inner diameter close to the tip diameter. One side of the tip can be filled with the amount of absorbing centers sufficient for one initiation. The tube can be made of a fibrous material on the inner surface and can be used for tip cleaning during the $2^{nd}$ stage of initiation.

Instead of user-performed initiation on-site, the tips may be supplied factory initiated. In this case, a delivery system should have quick connection, where changeable tips are inserted (reusable or disposable). Some of the possible embodiments for the delivery system with changeable tips are described here in FIGS. 15(*a*)-(*h*). Laser handpiece includes a housing 1501 and the optical fiber 1502 in which enters the laser radiation. The output of optical fiber is optically coupled with the tip using an optical element 1503. Optical element

1503 can be a regular or gradient lens. Alternatively couple coupling can be made via direct contact between the fiber and the tip. The optical system may be comprised of one or more lenses. Lenses may be spherical or aspherical. The material of the optical element 1503 can be used in homogeneous optical materials such as quartz, sapphire, garnet, etc., as well as composite (heterogeneous) agents, such as fused silica containing metal oxides (Cr, Fe, Nd, etc.).

Figure 15:
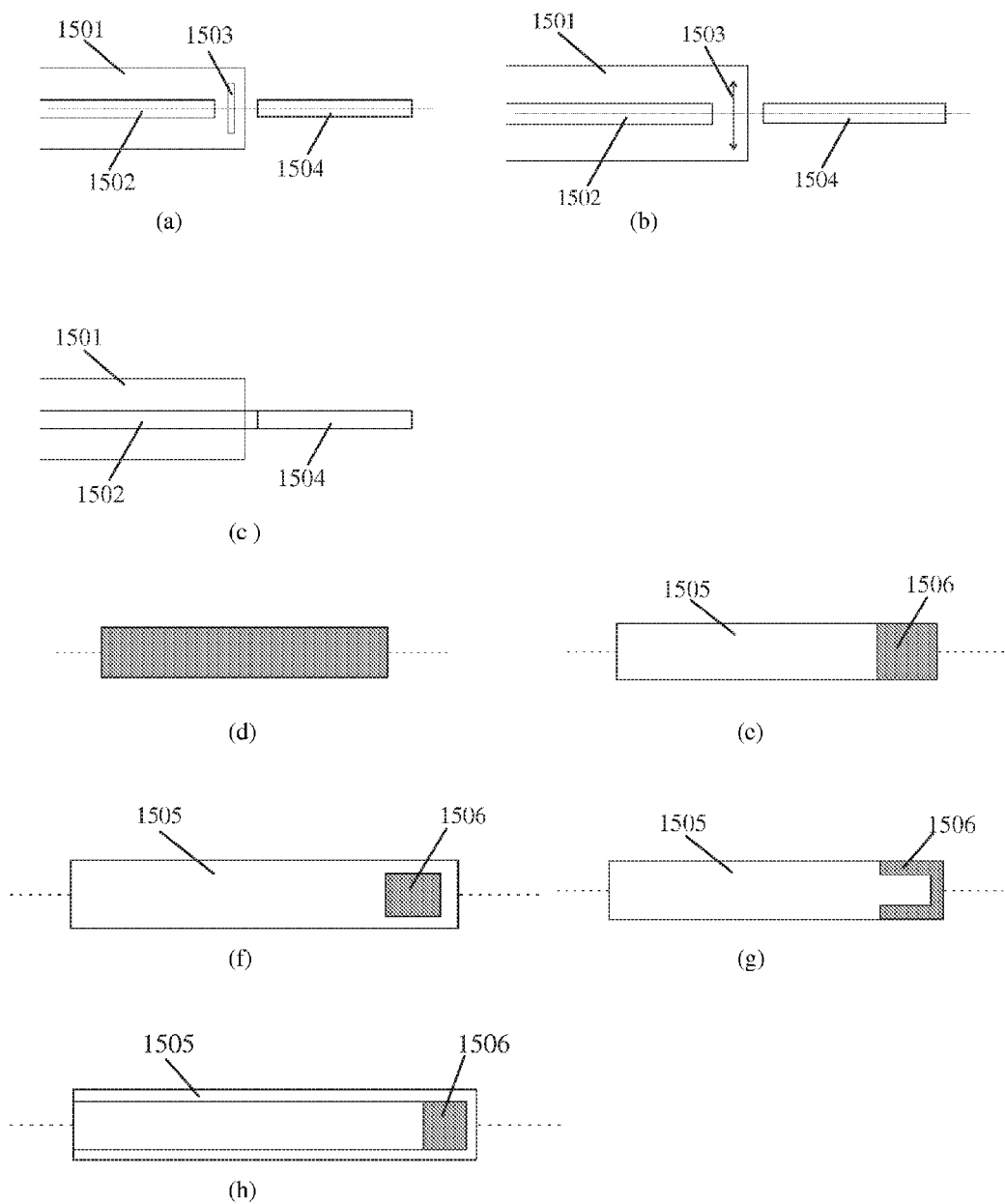
FIGS. 15(a)-(h) show embodiments of TOT initiation.

The factory initiated tip may consist of optically absorbing material or it may be a piece of optically transparent material with absorbing substance at the distal end of the tip. Several possible configurations for factory initiated tips are presented in FIGS. 15*d* to *h*. The tip may have different shapes-cylinder, cone, sphere, plate, polyhedron, etc. FIG. 15*d* shows a cylinder comprised of an absorbing material. FIG. 15(*e*) shows a transparent cylinder with distal part 1506 made of a absorbing material. The absorbing material may occupy just a part of the cross-section, as shown in FIG. 15(*f*). FIG. 15 (*g*) shows an embodiment when absorbing material envelops the transparent tip. FIG. 15(*h*) shows an embodiment where transparent tip and absorbing material are placed in a tube with close end to hold them together mechanically. TOT can be prepared by sintering or thermal bonding of absorption centers in an oven with a precise temperature control to achieve the result equivalent to $1^{st}$ and $3^{rd}$ stages of initiation.

The described methods and apparatuses of tip initiation provide more consistent absorption of TOT. An absorption of initiated tip A or tip transmission T=(1-A) can be in the range for A=0.05- 1 and for T=0-0.95, preferably range for A=0.5-1 and for T =0-0.5.

Higher value of A, such as 0.7-1, may be important when heating of tissues or nearby structures by scattered laser radiation and should be avoided. In particular, surgery around implants should not lead to overheating of implant and damage of surrounding tissues, including bone and soft tissues.

$T_{TOT}$ is determined by A and laser power P, if $T_{TOT}$ is below temperature of thermally induced absorption $T_{TIA}$ of the tip material. Thermally induced absorption of dielectric of tip material $A_{TIP}$ (T) is due to increasing concentrations of free electrons and others mechanisms. For example, for quarts $T_{TIA}$ is about 1000° C. For sapphire $T_{TIA}$ is about 1800° C. Light absorption of the tip material is increased if $T_{TOT}>T_{TIA}$ and total coefficient absorption k=A+$A_{TIP}$(T) is increased and $A_{TIP}$(T) is distributed in the volume of tip. Operation with $T_{TOT}<T_{TIA}$ is preferable for a more accurate regulation of $T_{TOT}$ and control of the cutting process. Operation with $T_{TOT}>T_{TIA}$ is preferable for using TOT as convertor of laser radiation in incandensent radiation due to high efficiency of converting and emitting of incandescent radiation from larger volume of TOT, where thermally induced absorption of the tip material is occurring.

Automatic power control (APC) mode of tissue cutting, vaporization, ablation and coagulation with TOT and TOT initiation require realtime measurement of the tip temperature. Realtime measurement of the TOT temperature can be performed by detection of heat (incandescent) radiation from the TOT or photoacoustic, fluorescence or other signal from the TOT which is dependent on $T_{TOT}$.

Figure 16:
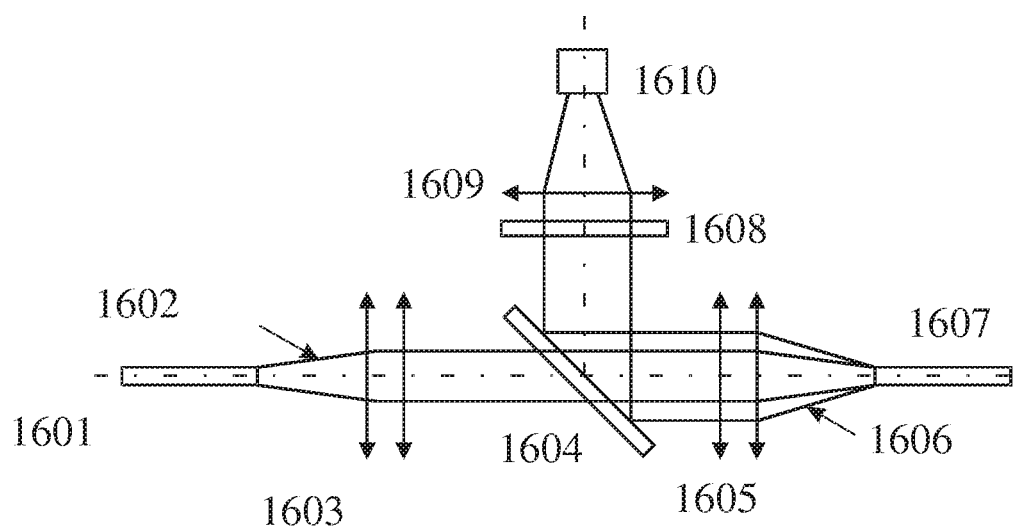
FIG. 16 is a schematic illustration of optical layout for temperature measurement.

Optical layouts for detection of heat radiation allowing detection of thermal signal are shown in FIG. 16. The radiation of treatment laser may have divergence close to diode laser, may be collimated or injected into an optical fiber. In this embodiment, the radiation of the treatment laser 1602 is injected into the optical fiber 1601. The divergence of laser radiation at the fiber output is determined by numerical aperture (NA) of the fiber 1607.

Laser radiation from input fiber output goes to collimator 1603, passes through spectral beam splitter 1604 and is focused by collimator 1605 onto input of optical fiber 1607 delivering laser radiation to the tip and tissue (not shown). Thermal signal appears while heating of the TOT by laser radiation and propagates along the output fiber in the direction opposite to the direction of laser radiation propagation. If the NA of the output fiber is higher than the angular divergence of injected laser radiation then the angular divergence of thermal signal will be more than of laser radiation. After leaving the output fiber, thermal signal passes through collimator 1605, reflects from spectral splitter 1604, passes through filter 1608 and is focused by lens 1609 on photodetector 1610. Photodetector 1610 can be made of Si, Ge or GaAlAs. For example, multiple photodiodes produced by Hamamatsu Photonics can be used for the registration system.

Figure 17:
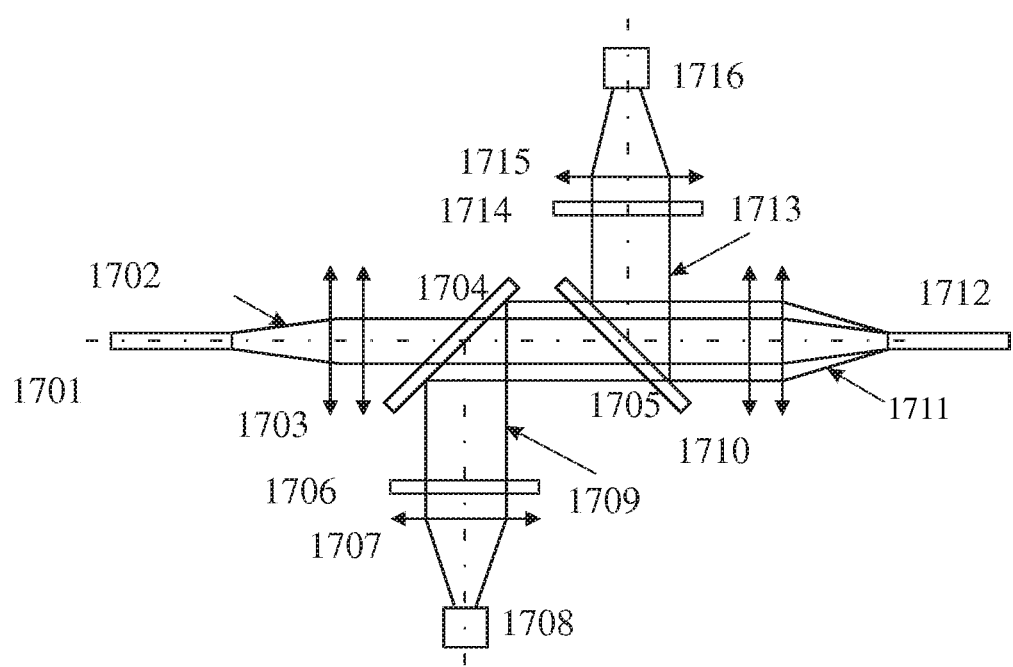
FIG. 17 is a schematic illustration of alternative optical layout with simultaneous registration of light reflection or fluorescence.

In another embodiment, heat radiation is detected simultaneously or sequentially with optical radiation propagating through same output fiber as shown on FIG. 17. This optical signal, together with a thermal one, is coupled into the output fiber 1712 and propagates along the fiber in the direction opposite to the direction of propagation of main laser radiation. Output fiber 1712 for measuring heat radiation can be made of quartz, sapphire; germinate glass, fluoride glasses, or hollow fiber. A system and device for TOT temperature control is a part of a surgical laser. The same system can be a part of TOT preparation device which is comprised of a fixture for TOT, absorbing element and tip cleaning system. The device for TOT preparation can be a part of the surgical laser with dual used TOT temperature control system. Beam splitter 1705 with filter 1714 and lens 1715 and photodetector 1716 are used for the detection of heat radiation signal and measurement of temperature of TOT and tissue. Beam splitter 1704 with filter 1709, lens 1707 and photodiode 1708 are used for detection of optical signal. Optical signal can be back reflected main laser radiation from TOT. At least one additional laser or LED radiation can be injected in the same output fiber and detected in the same channel or similar channel as 1704, filter 1709, lens 1707 and photodiode 1708. Additional lasers or LEDs can be emitting on different wavelengths. The same channel can be used for measurement of fluorescence from the tip or tissue. A fiber with double cladding can be used for better separation of thermal and optical signals.

In the layouts shown on FIGS. 16 and 17, the beam splitters 1604 or 1705 and filters 1608 or 1714 perform spectral separation between secondary (heat) radiation and reflected or scattered diode laser radiation. In addition to or instead of spectral separation, one can perform temporal separation between these optical signals. In particular, laser radiation can be pulsed and heat radiation can be measured only during the pause between pulses, when scattered and reflected laser radiation is not present and therefore doesn't interfere with the measurement process.

For optimal performance the pause between pulses should be preferably less than thermal relaxation time for the TOT, which could be between 0.001 ms and 500 ms, depending on the tip diameter and configuration. Thermal relaxation of TOT may be comprised of two components.

The first component is thermal relaxation of absorption centers and the other component is thermal relaxation of with the tip volume. Absorption centers are usually located in thin layer having a thickness in the range of 0.1-100 tm and thermal relaxation time in the range of about 0.001-10 ms. The second component is related to the thermal relaxation of the TOT as a whole. TOT has diameter in the range of 200-1000 tm and thermal relaxation time in the range of about 25-625 ms. Both temperatures of absorption centers and tip volume can be measured with the described method and apparatus in pause between laser pulses, which has to be about 10-625 ms. The temperature of absorption centers should be measured during the first 0.001-10 ms. The temperature of tip volume should be measured during the interval after first measurement and up to 625 ms. Based on this measurements, either of these temperatures can be regulated or maintained separately. For example, measurement of the whole tip volume temperature can be used to prevent thermally induced tip absorption by limiting laser power.

In yet another embodiment, separation between thermal and optical signal can performed without beam splitter. In this embodiment, apparatus for backward signal measurement include input for laser radiation optical separator and optical waveguide (for example, optical fiber) for delivery radiation to the tip and backward heat radiation and optionally optical signal from tissue or tip back to the optical separator. In this embodiment, numerical aperture of laser radiation $NA_L$ which is coupled into the waveguide at least in one direction is smaller than numerical aperture of waveguide (radiation guide) $NA_W$.

Optical separator can transmit radiation with numerical aperture smaller than $NA_L$ and reflect or deflect radiation outside of the numerical aperture $NA_L$. The separator may have reflective or refractive element for directing radiation from the output waveguide in angle which is higher than $NA_L$ but it is smaller than $NA_W$ to photodetector to measure backward radiation from the waveguide, which can be secondary radiation or reflected/backscattered radiation. For example, separator can be a lens partially covered with reflective coating. This lens serves several proposes, including transfer of radiation from input fiber with numerical aperture $NA_L$ optically coupled with the laser, to the second fiber with numerical aperture $NA_W$ delivering laser radiation to the tip and then reflection and secondary radiation back to photodetectors.

The device operates as follows. Laser radiation leaves the first optical fiber and enters the lens separator. Part of the radiation reflected from the front surface of the lens is collected by a focusing lens to the receiving area of the photodetector, which serves as incident optical power monitor. Laser radiation is focused by the main lens to the second optical fiber (radiation guide) and propagates to the tip and treating tissue. At the distal end of the second optical fiber or in the TOT laser radiation is partially converted into secondary radiation. Secondary radiation propagates back along the fiber, coming back to the lens separator. The first and second fibers may have different numerical apertures. Accordingly, radiation coming from these fibers has different divergencies $NA_L$ and $NA_W$. The lens separator has a reflective coating outside of input radiation aperture. The part of secondary radiation contained in the solid angle outside of initial radiation divergency falls on the reflective coating, reflected and partially focused by another lens to the receiving area of a photodetector receiving secondary radiation. Also, the output of the second optical fiber contains laser radiation partly reflected or backscattered from the tip and biotissue. This radiation is also reflected from the same reflective coating and collected by another lens to another photodetector.

Figure 18:
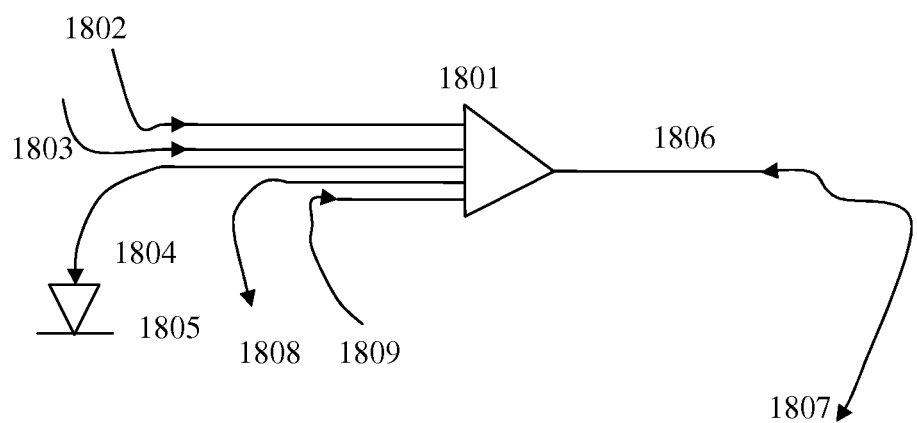
FIG. 18 is a schematic illustration of all-fiber optical layout with fiber combiner.

An optical schematic with functions similar to such schematics as shown in FIGS. 16 and 17 can be built based on an optical fiber combiner or integral optical elements. FIG. 18 shows an optical schematic of this embodiment. Laser radiation is coupled into fiber 1802 of optical fiber combiner 1801. Also, a pilot beam is coupled into another fiber 1803. The radiation is delivered to the tissue 1807 via output fiber 1806. Backward secondary radiation is measured in the output of fiber 1804 by photodetector 1805. Other channels of optical fiber combiner such as 1808 can be used for detection of back reflection laser radiation and such as 1809 for coupling of radiation from other auxiliary light source(s).

Optical properties of tissues (absorption, scattering) may be changed under influence of laser radiation. Thus, the reflected and backscattered signals on laser radiation wavelength may also change. This optical signal together with the thermal one are coupled into the output fiber and propagate along the fiber in the direction opposite to the direction of propagation of main laser radiation.

In addition, optical absorption of the tissue can be changed by adding an exogenous chromophore into or onto the tissue. For example, during sulcular debridement or decontamination it is possible to add some absorbing substance, such as black ink, into the periodontal pocket to increase heat production which may facilitate killing of bacteria. The temperature of this compound during laser irradiation can be measured using the same layout as for measurement of $T_{TOT}$.

The tip material, structure and, in particular, material refraction can be selected to provide strong light confinement to use only the most distal part for tissue treatment, or alternatively to provide controlled light leakage to the tissue, so that the tip can cut sideways for high speed, deep cutting, or can be used for side firing for uses such as endodontic canal sterilization. Both initial laser radiation and secondary radiation from the TOT can leak to the tissue. Also, tip with refraction close to the tissue will confine light well when not immersed into the tissue, however light will propagate sideways (leak) as soon as the tip immersed into the tissue. This light leakage can facilitate side cutting and limit optical power penetrating to the depth of tissue.

Optical channels can be used for measurement and control of several effects, such as tissue type detection, changing in the tissue induce by laser such coagulation, vaporization, carbonization. Optical channels can be used also for measurement of TOT conditions, damage and degradation, speed of movement in the tissue, depth of the tip in the tissue, a gap between the TOT and hard tissue, such as root or bone, when TOT is inside the mucosa.

Tissue detection can be based on measurement of back-reflection signal on several wavelengths. Examples include detection of epithelium, reticular or papillary layers of mucosa, bone, dentine and enamel or dental material. Laser power can be automatically adjusted for optimum effect on the treatment tissue. For example, additional lasers or LED operating in visible (red, green, blue) or near infrared range can be combined in the same fiber delivery system and then reflected light can be spectrally analyzed or separated in several spectral channels using filters or other optical elements and system can be calibrated for different tissue types by analyzing ratio between reflection or backscattering in different channels. For example, for detection of the type of tissue reflection signal on two wavelengths can be used. For example, one wavelength can be selected from the range of 300-600 nm with high absorption of blood and the other from the range with low blood absorption, such as 600-2000 nm, preferably 600-900 nm for differentiation of connective tissue or for differentiation of epithelium versus reticular or papillary layers of mucosa or soft tissue versus hard tissue. The same channel can be used for detection of carious base on high back scattering reflection of light from carious enamel or dentine. Preferable wavelength for caries detection can be selected from the range of 300-1300 nm, preferably 400-1100 nm range.

Optical channel can be used for detection of changes in tissue such as partial or full coagulation, ablation, carbonization and tissue depth coagulation measurement. For example, it is known that tissue scattering changes if tissue coagulation occurs. Therefore, real time control of scattering can be used to monitor the level of coagulation and shut down or change laser power after the coagulation reached some predetermined level. This can be used in particular to create coagulation columns or spots with predetermined parameters.

For many cuttings applications it is essential to have tip with at least partial absorption of laser, in other words, initiated or blackened tip. It is especially important for new infrared lasers with weak absorption in the biotis sue, in particular in the spectral range of 700-1200 nm. Lack of initiation will lead to high exposure of tissue with laser radiation with deep penetration to the tissue, which may lead to overheating and damage of significant volume of tissue. In a system with registration of secondary radiation from TOT it is possible to detect the absence or significant reduction of this secondary radiation because the tip is not initiated due to operator error, or the blackened portion broke during treatment. If the system is trying to maintain the tip temperature, which means to maintain some predetermined level of signal reading in secondary radiation detection channel, absence of tip absorption will result in "run away" of the closed loop system, producing unusually high laser power. If the "run away" is occurring, it can be detected as unusually low signal combined with unusually high laser power. Accordingly, the system may have a run away protection feature, shutting down the laser and prompting the user to verify the tip condition.

For some procedures the opposite situation takes place. These procedures should be performed using clean, uninitiated tip or fiber distal end, so only laser radiation should be emitted from a cold tip. In this situation it may be useful to detect unintentional blackening of the tip, for example, because of contamination or accidental contact with tissue. In such situation the system may have protection from unintended tip or contact tissue blackening or carbonization. If secondary radiation from the tip exceeds some predetermined threshold, the system can shut down the laser and/or prompt the user to verify the tip condition. Since under equal conditions the laser power required to maintain the predetermined temperature depends on the tip movement in the tissue, the changes in this power can be used to monitor tip movement speed, including detection of slowing down or stopping movement in the tissue. It is known that prolonged exposure of the tissue can increase collateral thermal damage and create strong coagulation and carbonization. Therefore, the same system which performs real time automated power control to maintain tip temperature can detect slow movement or stop and warn the operator or shut down laser radiation to prevent unnecessary tissue damage. Slowing down of handpiece movement can be detected by changes in power required to maintain $T_{TOT}$ or its time derivative dP/dt. When the movement sharply decelerates or stops, the power drops down because less power is needed to maintain the temperature with slower or zero speed. Other methods of tip movement speed assessment can be used such as force required to move the tip in the tissue using tenso-sensor, optical reflection/backscattering sensor, acoustic sensor, accelerometer and others.

Figure 19:
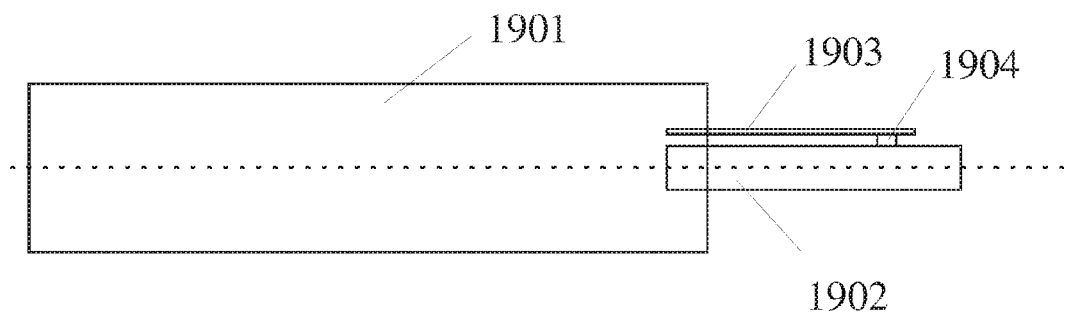
FIG. 19 is a schematic illustration of force measurement.

Another approach to speed monitoring is related to a tangential force required to move in the tissue during cutting. The speed is limited in particular by the tangential force resisting to the movement of tip in the biological tissue. This force varies in the process of cutting, because biological tissue is not uniform in its structure. The higher the force, the less speed is possible for the cutting. In some cases, the resistance of tissue can lead to destruction of the optical tip. Therefore, the force can be directly controlled with a sensor and laser power can be adjusted in real time to assure ability to continue cutting with intended speed. In a typical case, the tip is a cylinder with blackened distal end. During cutting the distal end is immersed in the biotis sue and experience tangential force during movement. One embodiment for force measurement element is shown in FIG. 19. The device consists of a laser handpiece 1901, the tip 1902, the load cell 1903 and fixture 1904. One end of the load cell 1903 is attached to the handpiece 1901 and the other through the fixture 1904 to the tip 1902. During cutting the tangential force is bending the tip and attached load cell. The load cell generates an electrical voltage proportional to the force. The relationship between tip temperature and laser power, as well as scattering of laser radiation, may change with tip depth in the tissue. Therefore, this depth can be monitored by registration of these signals and calibration of appropriate signals or ratios as a function of depth.

Optical channel can be used to measure the gap between the TOT and hard tissue, such as root or bone, when TOT is inside the mucosa. The scattering level or spectrum may change of a tip immersed in a soft tissue, is approaching hard tissue, such as tooth or bone. This may be detected by monitoring of backscattering or reflection of main laser radiation entering back to the optical fiber or by adding auxiliary laser source(s) at different wavelength and comparing ratio of two or more optical signals registered coming back from the optical fiber. For wavelength in the range of 300-2500 nm, preferably 300-1300 nm, the backscattering signal from hard tissue can be significantly higher than for mucosa. These differences can be used for detection of gap between hard tissue and tip immersed into soft tissue.

Optical channel can be used to measure presence of bacteria in hard tissue periodontal pocket, root canal and detection of calculus on the root.

Laser radiation can excite fluorescence which may be detected and serve as indication of bacterial film or other organic contamination. The same fiber which is used for laser treatment may be used to deliver light to excite fluorescence, which may be laser treatment light or auxiliary source light, and to collect fluorescence radiation coming back to the optical fiber and registered at the proximal end of the fiber, fluorescence signal can be excited by laser or LED with wavelength 300-1000 nm. This radiation can be delivered through optical schematic similar to pilot laser. Excitation laser can be CW or has pulse width shorter than fluorescence decay time. Registration of fluorescence can be performed after laser pulse. Optical channel which can be used to measure TOT temperature contains a fluorescent substance and detection system measures fluorescence signal emitted from the TOT. The fluorescence radiation partially propagates back through the optical fiber and is detected by the photosensor. The peak of fluorescence radiation can experience spectral shifting due to changes of the temperature of fluorescent substance in the tip.

TOT can be used for converting light energy to acoustic energy. Tissue water contacting to absorber on the tip can be heated to vaporization temperature with bubble formation. The bubble can generate positive and negative pressure in the tissue (acoustic waves). Acoustic waves can have a strong therapeutic effect such as tissue cutting, destruction of calculus on the root, stimulation of cell activities in a bone and vascular system in periodontal ligament and stimulate periodontal reattachment. During bubble formation on the absorber, temperature of the tip is changing and this change can be measured with a feedback control system described above. Laser power can be regulated based on this signal. Using $T_{TOT}$ control system, bubble formation and parameter of acoustic energy can be controlled and optimized for best treatment results. Same parameters can be measured using acoustic sensor acoustically coupled with the TOT or treatment zone of tissue. Acoustic signal can be used for the control of tissue treatment process. Acoustic or photo acoustic signals can be used for tissue type detection and tissue ablation registration.

In addition to heat conduction from TOT, laser radiation, which partially penetrates the biological tissue and is partially converted into infrared radiation, is absorbed in biotissue. In this case, biological tissue is heated. When heating tissue to temperatures above 100° C. the liquid contained in the tissue boils and starts formation of bubbles. When reaching critical size, bubbles collapse and forma wave of low pressure capable of destroying bacteria and their surrounding tissue. The above scenario can be used in the treatment of periodontal disease, namely, irradiation inside the gingival sulcus in order to secure the tooth structure to reduce the concentration of pathogenic bacteria by thermal destruction. Thermal distraction of the bacteria could be achieved when temperature of bacteria is raised to 50-80° C. Safety is ensured by the fact that the temperature at the surface of the tooth root is less than the critical value for odontoblasts injury.

Laser heat production may be associated with endogenous chromophores inside the sulcus or with exogenous chromophores. Such exogenous chromophores may be, for example, an aqueous suspension of carbon particles, including carbon particles and nanoparticles, gold particles, organic molecular, such as edible dyes, low phototoxixity dye, such as methylene blue, indocyanine green and others. For example, carbon particles may have size from about 10 nanometers to 200 µm. Preferable size in 0.1-5 µm. Carbon particles can be coated or encapsulated in biopolymer for easy penetration in periodontal pocket or selective attachment to bacteria or biofilm. Concentration of chromophore can be optimized to provide maximal heating effect on the bacteria with ensured safety of surrounded tissue. The concentration is selected from a range which provides coefficient of absorption on light wavelength in a range 10-10000 $cm^-$, preferably 250-5000 $cm^{-1}$. Before laser treatment, a compound with exogenous chromophore is applied inside periodontal pocket using a brush, a syringe or other applicator.

Figure 20:
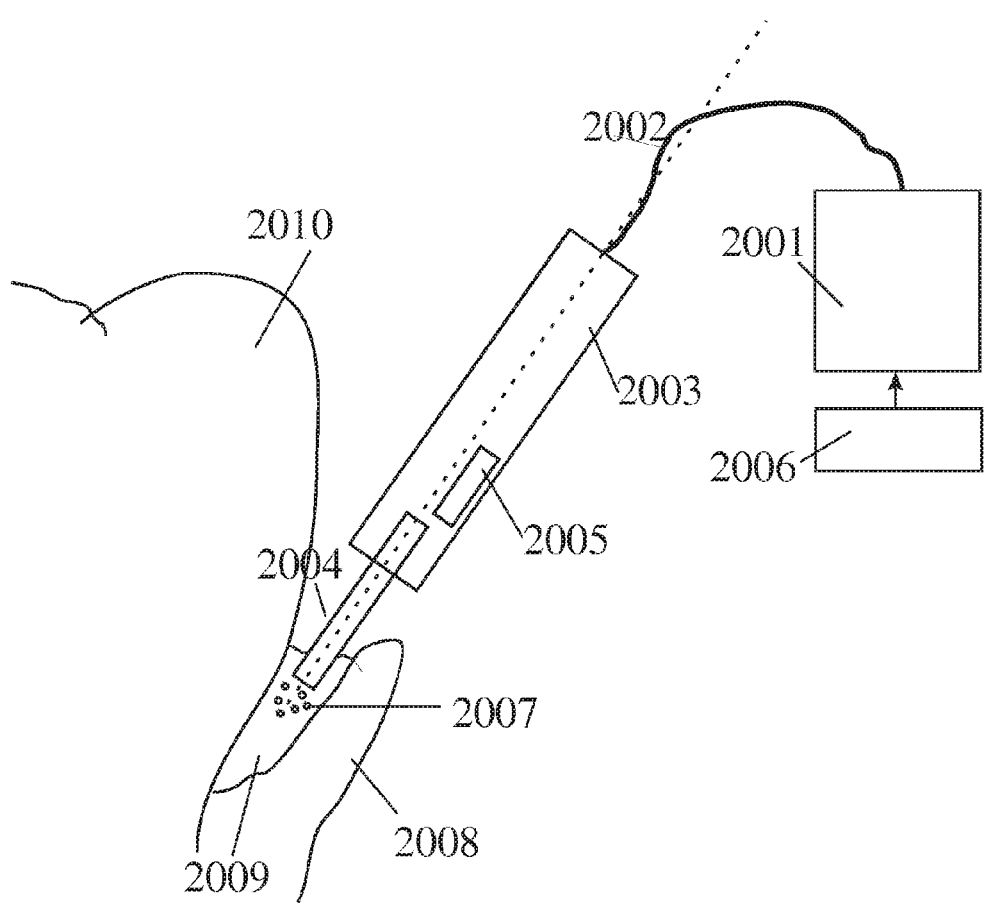
FIG. 20 is a schematic illustration of method of the invention.
Figure 21:
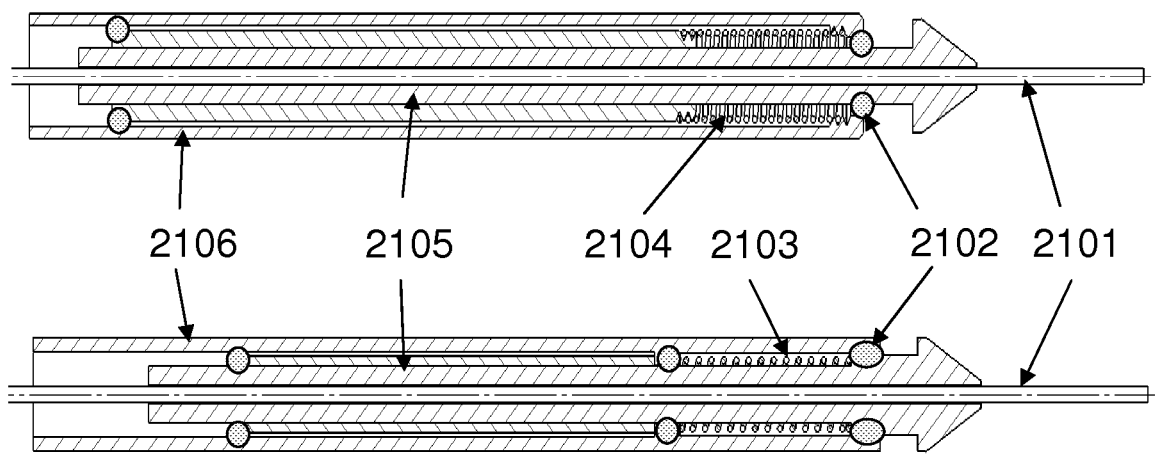
FIG. 21 is a schematic illustration of spring-loaded handpiece to maintain mechanical vertical force.

A method of treatment of periodontal disease consists in the treatment of gingival pocket laser wherein the laser radiation is terminated some time after the formation of gum pockets of cavitation bubbles and resumed as soon as these bubbles disappear. For the implementation of the method used by the device see FIG. 20. The device consists of laser 2001, delivery systems 2002, handpiece 2003, and a tip 2004. The tip 2004 can have absorption 0.05<A<0.7, preferably 0.05<A<0.3 or most preferably to be an optical tip with no absorption. The temperature of absorber and chromophore (for example carbon particles) is measured using heat radiation from chromophore or with optical system described above. Treatment of bacteria in periodontal pocket can be controlled by an acoustic sensor 2005 acoustically coupled with the tip 2004 whose output is used to adjust the laser power through control system 2006.

The device operates as follows. Laser radiation from a laser 2001 of the delivery system 2002 with a handpiece 2003 through the tip 2004 is delivered into the gingival sulcus. Absorption of laser radiation produces heating of bacteria and in addition bubbles, and generates acoustic waves. Temperature of tissue contacting with tip 2004 is measured based on secondary heat radiation which propagates back to measuring module (FIG. 16 for example) in control system 2006. As soon as the temperature achieves a safe limit, the laser power can be adjusted or shut down. Acoustic waves are measured by the acoustic sensor 2005 whose signal is transmitted to the control system 2006. As soon as bubble formation is acoustically detected, the laser power can be adjusted or shut down. The formation of bubbles stops, the acoustic wave disappears and the laser power is resumed.

The optical or thermo optical tip in contact mode has to be applied to tissue with certain mechanical force. This mechanical force is changed by the operator, due to changes in the speed of movement and mechanical properties of a tissue and laser power. The optimum range of mechanical force may depend on the tip design (diameter for example) and tissue properties. Mechanical force can be in the range from 0.5 to 30 grams, preferably 2-10 grams for vertical direction and 5-20 grams for horizontal directions. To provide consistent mechanical force from the hand of the operator to tissue, a laser handpiece with mechanical force optimization has been proposed. A schematic of an embodiment of such handpiece is shown in FIG. 14. Thermo-optical or optical tip 1401 is mounted in holder 1405. This holder is mechanically connected with a handpiece body 1406 through springs 1402, 1403, and 1404 with predetermined elasticity. The vertical spring 1404 extends while 1403 compresses the spring. The horizontal spring can be made as an O-ring. The springs may include a force sensor. The handpiece can be attached to an accelerometer. Signal from the force sensor or accelerometer can be used for control of laser power.

Other Embodiments

While the invention has been described in conjunction with the detailed description thereof, the foregoing description is intended to illustrate and not to limit the scope of the invention, which is defined by the scope of the appended claims. Other aspects, advantages, and modifications are within the scope of the following claims. The use of "such as" and "for example" are only for the purposes of illustration and do not limit the nature or items within the classification.

What is claimed is:

1. A surgical laser device comprising:
   a source of laser radiation optically coupled to a radiation guide having a proximal end and a distal end, the radiation guide serving to conduct the laser radiation between the proximal end and the distal end;
   the proximal end of the radiation guide serving to receive the laser radiation from the source;
   the distal end comprising a thermo-optical tip having absorption in the range of 0.5 to 1 serving to at least partially absorb the laser radiation, heat the thermo-optical tip with the laser radiation to a temperature ranging from 800 K to 1500 K and emit heat radiation indicative of the temperature of the thermo-optical tip;
   means to conduct the heat radiation from the distal end to the proximal end;
   a detector optically coupled to the proximal end for receiving the heat radiation and generating an output signal indicative of the temperature of the thermo-optical tip; and
   means responsive to the output signal for real-time controlling the source of the laser radiation to maintain the temperature of the thermo-optical tip at a predetermined level between 800 K and 1500 K for cutting biological tissue and maintaining a coagulation zone around a cut.

2. The surgical laser device of claim 1, wherein the tip is detachable.

3. The surgical laser device of claim 1, wherein a wavelength of the laser radiation ranges from 190 nm to 11000 nm.

4. The surgical laser device of claim 1, wherein a wavelength of the laser radiation ranges from 400 nm to 2700 nm, or from 800 nm to about 2100 nm.

5. The surgical laser device of claim 1, wherein the radiation guide is an optical fiber.

6. The surgical laser device of claim 5, wherein the optical fiber is a bare optical fiber end adapted to at least partially absorb the laser radiation on the distal end to create a thermo optical tip.

7. The surgical laser device of claim 1, wherein the radiation guide is a hollow guide.

8. The surgical laser device of claim 1, wherein the detector is configured to register optical radiation having a wavelength ranging from 300 nm to 18000 nm.

9. The surgical laser device of claim 1, wherein the detector is configured to register optical radiation having a wavelength ranging from 1000 nm to 2700 nm.

10. The surgical laser device of claim 1, wherein the detector is configured to register the radiation having a wavelength ranging from 1300 nm to 2700 nm.

11. The surgical laser device of claim 1, wherein the detector is configured to register the radiation having a wavelength ranging from 300 nm to 1100 nm or from about 300 nm to 1500 nm.

12. The surgical laser device of claim 1, wherein the detector is configured to register the radiation having a wavelength ranging from 1500 nm to 2700 nm.

13. The surgical laser device of claim 1, wherein the predetermined level of the output signal corresponds to a predetermined temperature of the tip.

14. The surgical laser device of claim 1, wherein the predetermined temperature of the tip correlates with a predetermined size of a coagulation zone during treatment.

15. The surgical laser device of claim 1, wherein the radiation guide comprises an optical or hollow fiber with its proximal end receiving the laser radiation, its distal end being optically connected with the proximal end of the thermo optical tip, which distal end at least partially absorbs the laser radiation.

16. The surgical laser device of claim 1, wherein the tip comprises embedded absorption material.

17. The surgical laser device of claim 16, wherein the absorption material comprises carbon particles, metal ions, or metal oxides.

18. A surgical laser device comprising:
sources of light radiation comprising at least one laser source optically coupled to a radiation guide having a proximal end and a distal end and being adapted to conduct a laser radiation from at least one laser source between the proximal end and the distal end comprising a thermo-optical tip having absorption in the range of 0.5 to 1;
the proximal end of the radiation guide being adapted to receive the laser radiation from the at least one laser source;
means for conducting reflected and/or backscattered thermal radiation from the distal end to the proximal end;
a detector optically coupled to the proximal end for receiving the reflected and/or backscattered thermal radiation and for generating an output signal indicative of the temperature of the thermo-optical tip; and
means responsive to the output signal for real-time adjusting the power of the laser radiation to maintain the temperature of a thermo-optical tip between 800° K to 1500° K based on the output signal for cutting biological tissue and maintaining a coagulation zone around a cut.

* * * * *